United States Patent
Nagorsen et al.

(10) Patent No.: US 10,662,243 B2
(45) Date of Patent: *May 26, 2020

(54) DOSAGE REGIMEN FOR ADMINISTERING A CD19XCD3 BISPECIFIC ANTIBODY

(71) Applicant: AMGEN RESEARCH (MUNICH) GMBH, Munich (DE)

(72) Inventors: Dirk Nagorsen, Munich (DE); Peter Kufer, Munich (DE); Gerhard Zugmaier, Munich (DE); Patrick Baeuerle, Munich (DE)

(73) Assignee: AMGEN RESEARCH (MUNICH) GMBH, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/491,459

(22) Filed: Sep. 19, 2014

(65) Prior Publication Data

US 2015/0071928 A1 Mar. 12, 2015

Related U.S. Application Data

(63) Continuation of application No. 13/504,665, filed as application No. PCT/EP2010/066207 on Oct. 27, 2010, now Pat. No. 8,840,888.

(60) Provisional application No. 61/255,290, filed on Oct. 27, 2009.

(30) Foreign Application Priority Data

Oct. 27, 2009 (EP) ..................................... 09174104

(51) Int. Cl.
C07K 16/28 (2006.01)
A61K 39/00 (2006.01)
G01N 33/50 (2006.01)

(52) U.S. Cl.
CPC ...... *C07K 16/2809* (2013.01); *C07K 16/2803* (2013.01); *G01N 33/505* (2013.01); *G01N 33/5052* (2013.01); *G01N 33/5094* (2013.01); *A61K 2039/505* (2013.01); *A61K 2039/545* (2013.01); *A61K 2039/55* (2013.01); *C07K 2317/31* (2013.01); *G01N 2800/52* (2013.01)

(58) Field of Classification Search
CPC ........ A61K 2039/545; A61K 2039/507; A61K 39/395; A61K 39/39558; C07K 16/2809; C07K 16/2803; C07K 2317/31
See application file for complete search history.

(56) References Cited

U.S. PATENT DOCUMENTS

| | | | |
|---|---|---|---|
| 8,007,796 B2 | 8/2011 | Baeuerle et al. | |
| 8,840,888 B2* | 9/2014 | Nagorsen | C07K 16/2803 424/135.1 |
| 10,191,034 B2* | 1/2019 | Nagorsen | C07K 16/2803 |
| 2009/0011455 A1 | 1/2009 | Warren et al. | |
| 2013/0095103 A1 | 4/2013 | Baeuerle et al. | |
| 2014/0199307 A1* | 7/2014 | Nagorsen | C07K 16/2803 424/135.1 |

FOREIGN PATENT DOCUMENTS

| | | |
|---|---|---|
| CN | 1299410 A | 6/2001 |
| CN | 101331151 A | 12/2008 |
| JP | 2002-512020 A | 4/2002 |
| JP | 2009-519257 A | 5/2009 |
| JP | 2014 513088 A | 5/2014 |
| WO | WO-1999/54440 A1 | 10/1999 |
| WO | WO-2004/106381 A1 | 12/2004 |
| WO | WO-2007/068354 A1 | 6/2007 |
| WO | WO-2008/119565 A2 | 10/2008 |
| WO | WO-2008/119567 A2 | 10/2008 |
| WO | WO-2010/052014 A1 | 5/2010 |
| WO | WO-2012/146394 A1 | 11/2012 |

OTHER PUBLICATIONS

Bargou et al., Tumor regression in cancer patients by very low doses of a T cell-engaging antibody, *Science* 321:974-97 and Supporting Online Material (2008).
Crick F.H.C., Codon-anticodon pairing: The wobble hypothesis, *J. Molec. Biol.* 19(2): 548-55 (1966).
Dubois et al., Clinical Calorimetry, Tenth Paper, A formula to estimate the approximate surface area if height and weight be known, *Arch. Intern. Med.* 17:863-71 (1916).
Gehan Ea., Estimation of human body surface area from height and weight, *Cancer Chemother. Rep.* 54(4):225-35 (1970).
International Search Report, dated Jan. 13, 2011, in related International Patent Application No. PCT/EP2010/066207.
Leandro et al., Reconstitution of peripheral blood B cells after depletion with rituximab in patients with rheumatoid arthritis, *Arthritis & Rheumatism* 54(2) 613-20 (2006).
Molhoj et al., CD19-/CD3-bispecific antibody of the BiTE class is far superior to tandem diabody with respect to redirected tumor cell lysis, *Mol. Immunol.* 44:1935-43 (2007).
Mosteller RD., Simplified calculation of body-surface area, *N. Engl. J. Med.* 317(17):1098 (1987).

(Continued)

*Primary Examiner* — Jessica H Roark
(74) *Attorney, Agent, or Firm* — Marshall, Gerstein & Borun LLP

(57) ABSTRACT

The disclosure provides a method for assessing the risk of potential adverse effects for a human patient mediated by the administration of a CD19×CD3 bispecific antibody to said patient comprising determining the ratio of B cells to T cells of said patient. The disclosure also provides a method for administering a CD19×CD3 bispecific antibody to a human patient having a B:T cell ratio of about 1:5 or lower, comprising administering doses in a dosing regimen. This dosing regimen can be applied in methods for treating malignant CD19 positive lymphocytes or for ameliorating and/or preventing an adverse effect mediated by the administration of said bispecific antibody. The Also provided is a pharmaceutical package or kit comprising a first dose and a second dose and optionally a third dose of said antibody.

20 Claims, No Drawings
Specification includes a Sequence Listing.

(56) References Cited

OTHER PUBLICATIONS

Needleman et al., A general method applicable to the search for similarities in the amino acid sequence of two proteins, *J. Mol. Biol.* 48:443-453 (1970).
Schlereth et al., T-cell activation and B-cell depletion in chimpanzees treated with a bispecific anti-CD19/anti-CD3 single-chain antibody construct, *Cancer Immunol. Immunother.* 55:503-14 (2006).
Smith et al., Comparison of Biosequences, *Advances in Applied Mathematics* 2(4):482-9 (1981).
Matthias Klinger, [Mode of Action of the Bispecific Anti-CD19 × Anti-CD3 Bite Antibody MT103 in Patients with Relapsed Indolent B-cell non-Hodgkin Lymphoma], Dissertation, Eberhard Karls University, Tuebingen, Germany, dated Jan. 1, 2009. English translation (pp. 1-107) of German dissertation (pp. 108-221).
Hoffmann et al., Serial killing of tumor cells by cytotoxic T cells redirected with a CD19-/CD3-bispecific single-chain antibody construct, *Int. J. Cancer*, 115(1):98-104 (2005).
Loffler et al., Efficient elimination of chronic lymphocytic leukaemia B cells by autologous T cells with a bispecific anti-CD19/anti-CD3 single-chain antibody construct, *Leuk.* 15(5):900-9 (2003).
Nagorsen et al., Immunotherapy of lymphoma and leukemia with T-cell engaging BiTE antibody Blinatumomab, *Leuk. Lymph.* 50(6):886-91 (2009).
Argouges et al., Combination of rituximab with blinatumomab (MT103/MEDI-538), a T cell-engaging CD19-/CD3-bispecific antibody, for a highly efficient lysis of human B lymphoma cells, *Leuk. Res.*, 33(3):465-73 (2008).

\* cited by examiner

DOSAGE REGIMEN FOR ADMINISTERING A CD19XCD3 BISPECIFIC ANTIBODY

The present invention relates to a method for assessing (analyzing) the risk of potential adverse effects for a human patient mediated by the administration of a CD19×CD3 bispecific antibody to said patient comprising determining the ratio of B cells to T cells of said patient, wherein a ratio of about 1:5 or lower is indicative for a risk of potential adverse effects for said patient. Accordingly, the present invention relates a method (dosage regimen) for administering a CD19×CD3 bispecific antibody to a human patient having a B:T cell ratio of about 1:5 or lower, comprising (a) administering a first dose of said antibody for a first period of time; and consecutively (b) administering a second dose of said antibody for a second period of time, wherein said second dose exceeds said first dose. In some embodiments, a third dose of said antibody is administered for a third period of time. This dosage regimen can be applied in methods for treating malignant CD19 positive lymphocytes or for ameliorating and/or preventing an adverse effect mediated by the administration of said bispecific antibody. The present invention also relates to the use of a CD19×CD3 bispecific antibody for the preparation of a pharmaceutical composition to be used in a method of the present invention. A pharmaceutical package or kit comprising a first dose and a second dose and optionally a third dose of said antibody as defined in the methods/dosage regimen of the present invention is disclosed as well.

Antibody-based cancer therapies require a target antigen firmly bound to the surface of cancer cells in order to be active. By binding to the surface target, the antibody can directly deliver a deadly signal to the cancer cell or indirectly by, for example, recruiting a cytotoxic T cell, if it is a bispecific antibody. In an ideal treatment scenario, a target antigen is abundantly present and accessible on every cancer cell and is absent, shielded or much less abundant on normal cells. This situation provides the basis for a therapeutic window in which a defined amount of the antibody-based therapeutic effectively hits cancer cells but spares normal cells.

Though antibodies are an effective means in treating many disorders, in particular cancer, their administration is not necessarily devoid of side effects. Adverse effects may cause a reversible or irreversible change in the health status of a patient. As adverse effects could be harmful and undesired, it is highly desirable to avoid them. However, though it is known that a medicament can cause adverse effects, its prescription and administration could not be avoided or is accepted, since the medicament has an outstanding beneficial therapeutic effect or may even be life-saving.

In clinical trials, a general distinction can be made between adverse effects (AEs) and serious adverse effects (SAEs). Specifically, adverse effects can be classified in 5 grades in accordance with the Common Terminology Criteria for Adverse Events (CTCAE). Grade 1 relates to mild AE, Grade 2 to moderate AE, Grade 3 to severe AE, Grade 4 to life-threatening or disabling AE, while Grade 5 means death related to AE.

An adverse effect observed in antibody therapy is the occurrence of infusion-related side effects, such as the cytokine release syndrome ("CRS"). Other adverse side effects described to be associated with CRS are fatigue, vomiting, tachycardia, hypertension, back pain, but also central nervous system reactions (CNS reactions), such as seizures, encephalopathy, cerebral edema, aseptic meningitis, and headache.

Cytokine release and neurological reactions have not only been observed with monoclonal antibodies binding to the T cell receptor but also with a CD19×CD3 bispecific single chain antibody binding to the CD3 part of the T cell receptor (called Blinatumomab (MT103)).

Blinatumomab (MT103) is a lymphoma-directed, recombinant bispecific single-chain CD19×CD3 antibody that binds to CD19 on the surface of almost all B cells and B tumor cells and concomitantly can engage a T cell, thereby triggering the T-cell to kill the target B cell or B tumor cell. Blinatumomab consists of four immunoglobulin variable domains assembled into a single polypeptide chain. Two of the variable domains form the binding site for CD19, a cell surface antigen expressed on most B cells and B tumor cells. The other two variable domains form the binding site for the CD3 complex on T cells. Blinatumomab is designed to direct the body's cytotoxic, or cell-destroying, T cells against tumor cells, and represent a new therapeutic approach to cancer therapy. Blinatumomab is presently in clinical trials.

As described for instance in WO 99/54440, adverse effects have been observed in a previous study performed with Blinatumomab applied in repeated bolus infusions to a patient with B-cell derived chronic lymphatic leukaemia (B-CLL). As shown in FIGS. 19 and 20 of WO 99/54440, release of TNF, IL-6 and IL-8 has been found in response to each of the two administered 20 minute-infusions of 3 microgram and 10 microgram of the mentioned bispecific single chain antibody, respectively, with cytokine release after each administration. Maximal cytokine release was observed after administration of 10 microgram of bispecific single chain antibody. In a following clinical trial study, in which escalating doses of the CD19×CD3 bispecific single chain antibody have been administered to patients with B cell malignancies as bolus infusions, adverse effects have also been observed. According to a retrospective analysis, 7 out of 22 patients showed an early neurological reaction, including, for example, confusion, ataxia, speech disorder, or disorientation.

In order to try to better manage these undesired side effects, the mode of administration of the CD19×CD3 bispecific single chain antibody has been changed in that it has been switched over from bolus infusion to a continuous intravenous administration of said antibody for a longer period of time. As shown in Bargou et al. (Science 321 (2008): 974-7), doses as low as 0.005 milligrams per square meter per day continuously administered to non-Hodgkin's lymphoma patients over four weeks led to an elimination of lymphoma target cells in blood. Partial and complete tumor regressions were first observed at a dose level of 0.015 milligrams/m$^2$/d, and all seven patients treated at a dose level of 0.06 milligrams/m$^2$/d experienced a tumor regression (Bargou et al., cited above). The CD19×CD3 bispecific single chain antibody also led to clearance of tumor cells from bone marrow and liver. However, though this (still ongoing) study established clinical proof of concept for the therapeutic potency of the CD19×CD3 bispecific single chain antibody format in the treatment of blood-cell derived cancer, neurological reactions have been found in the course of the aforementioned clinical trial. Accordingly, since Blinatumomab is a very promising candidate medicament for treating non-Hodgkin's lymphoma (NHL), acute lymphoblastic leukemia (ALL), chronic lymphocytic leukemia (CLL) and/or mantle cell lymphoma, it is highly desirable to reduce or even completely avoid undesired side-effects in the treatment of patients in need thereof with the CD19×CD3 bispecific single chain antibody.

Evidently, it is difficult to design a CD19×CD3 antibody-based therapy, which does not cause CNS (neurological) reactions including neurological reactions, or, to put it differently, it is desired to provide a CD19×CD13 antibody-based medical therapies with increased patient tolerability, i.e., reduced or even no undesired adverse effects such as CNS reactions.

Though pharmaceutical means and methods which allow a more gradual activation of T cell populations (see WO 2007/068354) already helped to avoid significant adverse side effects in patients treated with the CD19×CD3 bispecific single chain antibody, neurological reactions could unfortunately not be prevented by these measures, in particular in cases in which doses of more than 5 to 10 microgram per square meter per day (i.e. 24 h) of the antibody have been administered.

Thus, the technical problem underlying the present invention was to provide dosage regimens and methods to overcome the above problem.

The present invention addresses this need and thus provides embodiments concerning methods as well as dosage regimens for administering a CD19×CD3 bispecific antibody to a human patient.

These embodiments are characterized and described herein and reflected in the claims.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

All publications and patents cited in this disclosure are incorporated by reference in their entirety. To the extent the material incorporated by reference contradicts or is inconsistent with this specification, the specification will supersede any such material.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

In view of the adverse events, particularly the CNS events including neurological reactions observed with antibodies, also including the CD19×CD3 bispecific antibody, the finding that the CD19×CD3 bispecific single chain antibody can be administered so that it is tolerated by the patients, if it is administered in accordance with the dosage regimen as provided herein, is definitely remarkable.

Specifically, the present inventors observed that those patients, to whom a CD19×CD3 bispecific antibody was administered, encountered CNS events, if they had a B:T cell ratio of about 1:5 or lower. Accordingly, the present invention for the first time establishes a low B:T cell ratio as a potential high risk factor for the occurrence of adverse effects including neurological reactions in the treatment of malignant CD19 positive lymphocytes occurring in leukemias and lymphomas (see Examples 2, 3 and 4).

Particularly, the inventors of the present application observed that non-Hodgkin lymphoma (NHL) patients and acute lymphoblastic leukemia (ALL) patients with a low B:T cell ratio in peripheral blood have an increased risk for the development of an early neurological reaction. This neurological reaction occurs mainly during the first day(s) of treatment with a CD19×CD13 bispecific antibody. In particular, the majority of the neurological reactions occurred after about 12 to 120 hours after start of treatment. These neurological reactions were transient, fully reversible and resolved without sequelae within 3 to 72 hours after stop of the treatment.

The inventors made these unexpected observations in various clinical trial studies using the CD19×CD3 bispecific antibody:

Looking at "short-term" (bolus) infusion trials, 7 out of 22 patients had an early neurological reaction. 6 of these 7 patients had a low B:T cell ratio, i.e., a B:T cell ratio of about 1:5 or lower, before treatment. Of the remaining 15 patients without neurological reaction, only 1 patient had a low B:T cell ratio.

In an NHL clinical trial (see Bargou et al., cited above), a total of 39 patients have been treated until August 2008. At this time point, it has been found that all patients with a neurological reaction that led to permanent discontinuation of the CD19×CD3 bispecific antibody treatment had a low B:T cell ratio (i.e., a B:T cell ratio threshold below 1:5). In particular, 5 neurological reactions have been observed in 10 patients with low B:T cell ratio (5/10), while no patient with a high B:T cell ratio (i.e., a B:T cell ratio higher than 1:5) had a neurological reaction that would have led to permanent discontinuation of CD19×CD3 bispecific antibody treatment (0/29).

Thereafter, a specific cohort for patients with low B:T cell ratio, i.e. an increased risk for early neurological reactions, was established in order to prospectively analyze the outlined theory and to specifically find mitigation steps for the patients at increased risk.

Since establishing these separated cohorts for high risk patients, 8 NHL patients were prospectively treated (data as of July 2009): 6 patients with low B:T cell ratio, 2 patients with high B:T cell ratio. Again no patient with a high B:T cell ratio had a neurological reaction, while 3 out of 6 patients with a low B:T cell ratio had a neurological reaction, leading to discontinuation of the treatment.

In sum, 69 NHL patients, including B-cell chronic lymphocytic leukemia (CLL) and mantle cell lymphoma (MCL), have been treated with a CD19×CD3 bispecific antibody, both with bolus infusion and continuous infusion:

Neurological reactions have been observed in 61% of the patients with low B:T cell ratio. In contrast, only 2% of the patients with high B:T cell ratio showed such adverse events (see the following examples).

In another clinical trial phase II study, 15 μg of CD19×CD3 bispecific single chain antibody per square meter patient body surface area per day have been administered to adult ALL patients by continuous infusion for at least four weeks. One out of 11 ALL patients of the high risk group having a B:T cell ratio below 1:5 showed a neurological reaction, leading to discontinuation of the treatment. In contrast, none of the 6 patients of the low risk group having a B:T cell ratio higher than 1:5 showed a neurological reaction.

Moreover, in a retrospective analysis of 39 NHL patients, a baseline B cell to T cell (B:T) ratio in peripheral blood at or below 1:5 to 1:10 was identified as the only predictive factor for the subsequent occurrence of neurological AEs. The predictive value was then prospectively confirmed in 8 additional patients (see Example 1).

In sum, these data establish a low B:T cell ratio, i.e., a B:T cell ratio of about 1:5 or lower as a potential high risk factor for the occurrence of adverse effects including neurological reactions in the treatment of malignant CD19 positive lymphocytes occurring in leukemia and lymphoma such as NHL, MCL, CLL and ALL in patients who are treated with a CD19×CD3 bispecific antibody (see Examples 1 and 4).

Thus, it was an aim of the present invention to provide a method that allows identifying patients who may be at a risk of suffering from adverse effects when being treated with a CD19×CD3 bispecific antibody. This method will improve drug compliance, since the identification of patients who are at a risk of suffering from adverse effects allows adjusting the dosage regimen of the CD19×CD3 bispecific antibody. In fact, the present inventors have applied their finding that a B:T cell ratio of about 1:5 or lower could be a potential risk factor for suffering from adverse effects in the treatment with a CD19×CD3 bispecific antibody and have thus developed a dosage regimen which is intended to prevent and/or ameliorate these adverse effects.

Accordingly, in a first aspect the present invention provides a method for assessing (analyzing) the risk of potential adverse effects for a human patient mediated by the administration of a CD19×CD3 bispecific antibody to said patient comprising determining in a sample from said patient the ratio of B cells to T cells of said patient, wherein a ratio of about 1:5 or lower is indicative for a risk of potential adverse effects for said patient.

"Assessing (analyzing) the risk" means that the method of the first aspect of the present invention aims at assessing or analyzing as to whether or not a patient has a higher or lower likelihood or probability (i.e., an increased or decreased risk, respectively) to encounter adverse effects. Accordingly, as is commonly known, a risk does not necessarily mean that a patient will or will not encounter adverse effects.

In the present invention, when a patient has a B:T cell ratio of about 1:5 or lower, said patient has (is at) an increased risk of potential adverse effects, also including the onset of an adverse effect, while a patient who has a B:T cell ratio higher than 1:5 does not have (is not at) or at least has (is at) a decreased risk of potential adverse effects, also including the onset of an adverse effect.

Accordingly, a B:T cell ratio of about 1:5 or lower is indicative for a risk of adverse effects, while a B:T cell ratio of higher than 1:5 is not indicative for a risk of adverse effects.

Thus, the term "indicative for" when used in the context of the method of the first aspect of the present invention means that a patient has an increased risk of potential adverse effects if the B:T cell ratio is about 1:5 or lower or has a decreased risk of potential adverse effects if the B:T cell ratio is higher than 1:5.

An "adverse effect" is a harmful and undesired effect resulting from medication in the treatment of a patient with a CD19×CD3 bispecific antibody. An adverse effect may also be termed a "side effect". Some adverse effects only occur only when starting, increasing or discontinuing a treatment. The inventors have observed that the adverse effect seen in the treatment of patients with a CD19×CD3 bispecific antibody occurred after about 12 to 120 hours after the start of the treatment and are reversible.

An adverse effect may cause medical complications. The inventors have observed neurological reactions in patients treated with a CD19×CD3 bispecific antibody. These neurological reaction, unless they can be stopped or avoided, lead to non-compliance with the CD19×CD3 bispecific antibody treatment.

However, as mentioned herein, the inventors found that the B:T cell ratio is an indicator as to whether or not patients are at a risk of potential adverse side effects. Specifically, a B:T cell ratio about or lower 1:5 is an indicator that patients are at a risk of potential side effects, while a B:T cell ratio higher than about 1:5 is an indicator that patients have no or at least have a decreased risk of potential side.

As mentioned before, the method of the first aspect of the present invention is for assessing (analyzing) the risk of adverse effects and a risk includes the assessment/analysis of likelihood or a probability. Accordingly, the term "potential" when used in the context of adverse effects means that— though a patient may have a B:T cell ratio of about 1:5 or lower—said patient does not necessarily have to encounter adverse effects.

Likewise, though a patient may have a B:T cell ratio higher than about 1:5—said patient does not necessarily have to not encounter adverse effects. Accordingly, the term "potential" implies that the method of the first aspect of the present invention provides predictions as to whether or not a patient may encounter adverse effects, but—self-explanatory as it is—cannot provide a 100% safe prediction, since, apart from the B:T cell ratio individual factors such as sex, age, weight, nutritional status, health status, pre-medication etc. may have an influence as to whether or not a patient will encounter adverse effects.

In accordance with the present invention an adverse effect is preferably characterized by a neurological reaction (also sometimes referred to herein as "CNS reaction" or "CNS event", for which reason these terms can be equally used). Said neurological reaction is preferably one or more selected from the group consisting of: confusion, ataxia, disorientation, dysphasia, aphasia, speech impairment, cerebellar symptoms, tremor, apraxia, seizure, grand mal convulsion, palsy, and balance disorder.

The degree of an adverse effect can, for example, be measured in accordance with the NCI Common Terminology Criteria for Adverse Events v3.0 (CTCAE) (Publish Date: Dec. 12, 2003) in grades. A Grade refers to the severity of the adverse effects. The CTCAE v3.0 displays grades 1 through 5 with unique clinical descriptions of severity for each adverse effects:

Grade 1: mild adverse effects
Grade 2: Moderate adverse effects
Grade 3: Severe adverse effects
Grade 4: Life-threatening or disabling adverse effects.
Grade 5: Death of the patient.

A "patient" is a human individual who will be or is treated with a CD19×CD3 bispecific antibody. In accordance with the present invention, the patient is suspected/assumed to comprise or already comprises malignant CD19 positive lymphocytes (in particular B cells). In the latter case, said patient has already been diagnosed to comprise such cells. These malignant CD19 positive lymphocytes (in particular B cells) are present in a patient developing and/or suffering from leukemia and/or lymphoma. In accordance with the present invention a patient is thus in need of a treatment of malignant CD19 positive lymphocytes. Preferably, a patient who will be or is treated with a CD19×CD3 bispecific antibody is (or has been) diagnosed in accordance with the method of the first aspect of the invention as described herein.

"Mediated by" when used in the context of the method of the first aspect of the present invention means that adverse effects that a patient may or may not encounter are caused by the administration of a CD19×CD3 bispecific antibody. Put it differently, the CD19×CD3 antibody is the causative agent that may cause potential adverse effects in a patient.

The administration may be in the form of a bolus administration or continuous administration, with continuous administration being preferred.

In accordance with the present invention by the term "sample" is intended any biological sample obtained from a human patient containing polynucleotides or polypeptides or portions thereof. Biological samples include body fluids (such as blood, serum, plasma, urine, saliva, synovial fluid and spinal fluid) and tissue sources found to malignant CD19 positive lymphocytes. Methods for obtaining tissue biopsies and body fluids from patients are well known in the art. Generally, a biological sample which includes peripheral blood mononuclear cells (PBMCs), in particular B cells and T cells is preferred as a source.

A sample which includes peripheral blood mononuclear cells (PBMCs), in particular B cells and T cells is preferably taken from peripheral blood of a human patient.

Other preferred samples are whole blood, serum, plasma or synovial fluid, with plasma or serum being most preferred. However, a sample from peripheral blood of a human patient is particularly preferred.

A "B:T cell ratio" as used herein refers to the ratio of the number of B cells and the number of T cells. It is preferably determined in a sample taken from a human patient. Preferably, the sample is taken from the peripheral blood of a human patient. The number of B or T cells, for example, in a peripheral blood sample can be determined by any means usually applied in the art, for example, by FACS analysis.

The B:T cell ratio is preferably about 1:5 or lower including a B:T cell ratio of about 1:6, 1:7, 1:8, 1:9, 1:10, 1:11, 1:12; 1:13, 1:14, 1:15, 1:20, 1:100, 1:200, 1:400, 1:500, 1:1000, 1:2000, 1:3000, 1:4000, 1:5000 or even lower, with 1:9 1:10, 1:50, 1:100, 1:500, 1:1000 being preferred, with 1:9 being particularly preferred.

"Determining the B:T cell ratio" includes
(a) determining the total B cell number in a sample from a patient, preferably in a peripheral blood sample of the patient;
(b) determining the total T cell number in sample from a patient, preferably in a peripheral blood sample of the patient;
(c) calculating the ratio of the B cell number of step (a) and the T cell number of step (b) in order to obtain a B:T cell ratio.

Of note, a low B:T cell ratio can also be seen as high T:B ratio; and vice versa. Accordingly, the ratios provided herein for a low B T cell ratio would then have to be reversed.

In contrast, patients showing a B:T cell ratio higher than about 1:5 (preferably 1:9), including a B:T cell ratio of higher than about 1:4, 1:3, 1:2, 1:1, 2:1, 3:1, 4:1, 5:1, 6:1, 7:1, 8:1, 9:1, 10:1 or higher, have a decreased risk of suffering from potential adverse effects upon administration of a CD19×CD3 bispecific antibody.

Accordingly, the present invention also envisages a method for assessing (analyzing) the risk of potential adverse effects for a human patient mediated by the administration of a CD19×CD3 bispecific antibody to said patient comprising determining in a sample from said patient the ratio of B cells to T cells of said patient, wherein a ratio of higher than about 1:5 (preferably 1:9) is indicative for a decreased risk of potential adverse effects for said patient.

Having observed that patients who have a B:T cell ratio of about 1:5 or lower are at an increased risk of potential adverse effects, the inventors developed a concept that allows the treatment of these patients with a CD19×CD3 bispecific antibody. Bearing this in mind, it has been elucidated that the T cells of such high risk patients have to be pre-adapted or partially activated by the administration of a low dose of antibody for several days before the dose can then be escalated. So it has been found that a significant decrease in dose given per time unit potentially increases tolerability to said antibody in the high risk patients.

In essence, the inventors found that "adapting" a patient to a CD19×CD3 bispecific antibody prior to the therapy with a CD19×CD3 bispecific antibody is beneficial for avoiding undesired adverse effect (particularly the unwanted neurological reactions) (see Examples 6 and 7).

Accordingly, the present invention relates in a second aspect to a method (dosage regimen) for administering a CD19×CD3 bispecific antibody to a human patient having a B:T cell ratio of about 1:5 or lower, comprising:
(a) administering a first dose of said antibody for a first period of time; and consecutively
(b) administering a second dose of said antibody for a second period of time;
wherein said second dose exceeds said first dose.

It will be understood that in the context of the present invention, the term "method" includes a "dosage regimen" to be used in a method of the present invention.

In the context of the present invention "administration of a CD19×CD3 bispecific antibody" or "administering a CD19×CD3 bispecific antibody" or any other grammatical form thereof means that the CD19×CD3 antibody is in the form of a pharmaceutical composition, optionally comprising a pharmaceutically acceptable carrier. Accordingly, it is to be understood that a pharmaceutical composition comprising a CD19×CD3 bispecific antibody is administered to a human patient.

The term "administering" in all of its grammatical forms means administration of a CD19×CD3 bispecific antibody (in the form of a pharmaceutical composition) either as the sole therapeutic agent or in combination with another therapeutic agent.

It is thus envisaged that the pharmaceutical composition of the present invention are employed in co-therapy approaches, i.e. in co-administration with other medicaments or drugs, for example, other medicaments for treating malignant CD19 positive lymphocytes in a patient and/or any other therapeutic agent which might be beneficial in the context of the methods of the present invention.

For example, if the methods of the invention are carried out for the treatment of B-lineage acute lymphoblastic leukemia or aggressive NHL, it can advantageously be combined with inthrathecal chemotherapy in order to eliminate target B cells from the CNS. For example, the inthratecal chemotherapy could be performed prior to the administration of the CD19×CD3 bispecific single chain antibody according to the methods described herein.

The administration of a pharmaceutical composition referred to herein is preferably an intravenous administration. It follows that in the methods of the present invention the route of administration in step (a) and/or the route of administration in step (b) is intravenous. It may be administered as a bolus injection or continually (continuously), with continually being preferred.

The administration of a CD19×CD3 bispecific antibody (for example in the form of a pharmaceutical composition) can be a bolus injection or continually or as also sometimes used herein continuously, with continually or continuously being preferred. A continual administration refers to an administration which is essentially without interruption. "Essentially without interruption" includes a continual administration usually without an uninterrupted flow or spatial extension.

In some embodiments, said first dose is not therapeutically active, i.e. it is a subtherapeutic dose. Without being strictly bound, for the purpose of the present invention a dose of 5 µg/m²/d or lower is held to be subtherapeutic.

In a preferred embodiment of the present invention the second dose is therapeutically active.

By "therapeutically effective amount" or "therapeutically active" is meant a dose of a CD19×CD3 bispecific antibody that produces the therapeutic effects for which it is administered.

The exact dose will depend on the purpose of the treatment, and will be ascertainable by one skilled in the art using known techniques. As is known in the art and described above, adjustments for age, body weight, general health, sex, diet, drug interaction and the severity of the condition may be necessary, and will be ascertainable with routine experimentation by those skilled in the art. The therapeutic effect of the respective methods or method steps of the present invention is additionally detectable by all established methods and approaches which will indicate a therapeutic effect. It is, for example, envisaged that the therapeutic effect is detected by way of surgical resection or biopsy of an affected tissue/organ which is subsequently analyzed by way of immunohistochemical (IHC) or comparable immunological techniques. Alternatively it is also envisaged that the tumor markers in the serum of the patient (if present) are detected in order to diagnose whether the therapeutic approach is already effective or not. Additionally or alternatively it is also possible to evaluate the general appearance of the respective patient (fitness, well-being, decrease of tumor-mediated ailment etc.) which will also aid the skilled practitioner to evaluate whether a therapeutic effect is already there. The skilled person is aware of numerous other ways which will enable him or her to observe a therapeutic effect of the compounds of the present invention.

In a third aspect, the present invention relates to a method for treating malignant CD19 positive lymphocytes in a human patient having a B:T cell ratio of about 1:5 or lower, said method comprising:
(a) administering a first dose of a CD19×CD3 bispecific antibody for a first period of time; and consecutively
(b) administering a second dose of said antibody for a second period of time;
wherein said second dose exceeds said first dose.

Malignant CD19 positive lymphocytes (in particular B cells) are found in leukemia and/or lymphoma. Accordingly, the CD19 positive lymphocytes are in a preferred embodiment lymphoma or leukemia cells.

"Malignant" describes lymphocytes (in particular B cells) that contribute to a progressively worsening disease, in particular lymphoma or leukemia and the diseases described herein. The term is most familiar as a description of cancer, here lymphoma and leukemia and the diseases described herein. Malignant CD19 positive lymphocytes (in particular B cells) are not self-limited in their growth, are capable of invading into adjacent tissues, and may be capable of spreading to distant tissues (metastasizing). Malignant when used herein is synonymous with cancerous.

However, as "normal" (non-malignant) lymphocytes (in particular B cells) also express CD19, it is to be expected that the CD19×CD3 bispecific antibody also binds these normal lymphocytes (in particular B cells) and upon recruiting cytotoxic T cells (because of the second specificity of the bispecific CD19×CD13 antibody) depletes these normal B cells. Yet, it is expected that the population of these normal B cells is reconstituted in the absence of the CD19×CD3 bispecific antibody. It was observed by Leandro and co-workers that after their depletion by an anti-CD20 antibody, B cells were reconstituted in rheumatoid arthritis patients (Arthritis Rheum. 2006 February; 54(2):613-20). As CD20, likewise CD19 is expressed on almost all B cells, it can be expected that B cells upon depletion by the bispecific CD19×CD3 antibody are reconstituted, too.

The lymphoma is preferably indolent or aggressive B cell non-Hodgkin lymphoma (B NHL), mantle cell lymphoma (MCL) or chronic lymphatic leukemia (CLL). Within the meaning of the invention, the term "B cell non-Hodgkin lymphoma" or "B cell derived non-Hodgkin lymphoma" comprises both indolent and aggressive B cell non-Hodgkin lymphoma (B NHL). The term "indolent or aggressive B cell non-Hodgkin lymphoma (B NHL)" as used herein represents malignant B cell-derived tumorous diseases. Indolent B NHL are low malignant lymphomas. Aggressive B-NHL are high malignant lymphomas. The B cell non-Hodgkin lymphoma (B NHL) may advantageously be a follicular lymphoma, lymphoplasmacytic lymphoma, marginal zone cell lymphoma, mantle cell lymphoma (MCL), diffuse large B cell lymphoma (DLBCL), Burkitt's lymphoma, small lymphocytic lymphoma (SLL/CLL) and any other B cell derived subtype. The term "B cell leukemia" as used herein may advantageously be any B cell leukaemia (e.g. chronic lymphocytic leukaemia or acute lymphocytic leukaemia). For further reference see e.g. http colon-backslash-backslash www.cancer.org. Preferably, indolent non-Hodgkin B cell lymphoma may be treated with a bispecific single chain antibody directed against both human CD3 and human CD19 as demonstrated in the following examples.

The leukemia is preferably B-lineage acute lymphoblastic leukemia (ALL).

In a fourth aspect, the present invention relates to a method for ameliorating and/or preventing an adverse effect mediated by the administration of a CD19×CD3 bispecific antibody to a human patient having a B:T cell ratio of about 1:5 or lower, said method comprising:
(a) administering a first dose of said antibody for a first period of time, and consecutively
(b) administering a second dose of said antibody for a second period of time;
wherein said second dose exceeds said first dose.

The adverse effect is preferably a neurological reaction, preferably one or more selected from the group consisting of: confusion, ataxia, disorientation, dysphasia, aphasia, speech impairment, cerebellar symptoms, tremor, apraxia, seizure, grand mal convulsion, palsy, and balance disorder (see also Examples 2 and 3).

Specifically, neurological reactions observed during the starting phase of treatment with the CD19×CD3 bispecific antibody include for example confusion and disorientation.

"Confusion" as used herein refers to loss of orientation which is the ability to place oneself correctly in the world by time, location, and personal identity, and often memory which is the ability to correctly recall previous events or learn new material. The patients usually have difficulties to concentrate and thinking is not only blurred and unclear but often significantly slowed down. Patients with neurological reactions also suffer from loss of memory. Frequently, the confusion leads to the loss of ability to recognize people and/or places, or to tell time and the date. Feelings of disorientation are common in confusion, and the decision-making ability is impaired. Neurological reactions further comprise blurred speech and/or word finding difficulties. This disorder may impair both, the expression and understanding of language as well as reading and writing. Besides urinary incontinence, also vertigo and dizziness may accompany neurological reactions in some patients.

The occurrence of neurological reactions in the treatment of B cell dependent lymphatic or leukemic malignancies with the CD19×CD3 bispecific antibody may be further influenced by the following factors:

1. Presence of Drug

The CD19×CD3 bispecific antibody retargets T cell cytotoxicity to malignant CD19 positive lymphocytes present, for example, in B cell lymphoma or leukemia cells. In light of this, it can be reasonably assumed that it is the presence of CD19×CD3 bispecific antibody in the body of a patient which is responsible for the adverse effects. Furthermore, side effects are observed only in parts of the body where the CD19×CD3 bispecific antibody is biologically active. Accordingly, neurological reactions upon treatment with the CD19×CD3 bispecific antibody are assumed to be dependent on the presence of said antibody in the cerebrospinal fluid (CSF; liquor) of the patient. This may be supported by the fact that the CD19×CD3 bispecific antibody as well as T cells have only been found in the CSF of NHL patients with a low B:T cell ratio. As explained herein, this patient population has an increased risk for the development of neurological reactions upon antibody treatment. This finding may suggest that the CD19×CD3 bispecific antibody is able to enter the perivascular space dividing the blood vessels and the CNS (including the brain), in high risk NHL and ALL patients. There, the CD19×CD3 bispecific antibody may then engage T cells to target local B cells (either benign or malign) which possibly leads to local cytokine release which in turn could cause neurological reactions.

2. Drug Dose

Further, the neurological reactions seem to be dependent on the dose of the CD19×CD3 bispecific antibody. For example, neurological reactions have not been observed upon continuous administration of 5 µg/m² body surface area of CD19×CD3 bispecific antibody, but with 15 µg/m² body surface area or more CD19×CD3 bispecific antibody in the high risk group of patients. For this reason, as mentioned herein, a dose of less than 5 µg/d/m² is deemed to be subtherapeutic. The effect of the drug dose is evident from the data shown in the appended examples. This observation may imply a dose dependency of neurological reactions in high risk patients with low B:T cell ratio.

3. Presence of Target Cells and Effector Cells

As set forth above, the neurological reactions upon CD19×CD3 bispecific antibody-treatment are assumed to depend on the presence of i) target cells, i.e. CD19-antigen carrying B cells and ii) effector cells, i.e. cytotoxically active T cells carrying the CD3 antigen, in the PVS/CNS.

In view of this, it is intriguing to hypothesize that the depletion of e.g. the target B cell from the PVS/CNS should result in the avoidance of neurological reactions. In fact, this is exactly what has been observed in the mentioned phase II study in which B lineage acute lymphoblastic leukemia (ALL) patients are being currently treated with the CD19× CD3 bispecific antibody:

In ALL, there is generally a high incidence of leukemic lesions in the CNS. Therefore, each of the ALL patients enrolled in the clinical phase II study referred to herein had received standard ALL therapies in the past, including methotrexate i.v. and/or intrathecal chemotherapy, in order to prevent central nervous system relapses. Some of them received in addition irradiation of the neuroaxis. The ALL patients thereafter received a consolidation therapy, i.e. they obtained several four week-treatment cycles of continuous administration of 15 µg/d/m² of CD19×CD3 bispecific antibody. Only one of the thus far enrolled 17 ALL patients who have been treated with the CD19×CD3 bispecific antibody has developed neurological reactions. This patient was one out of 11 patients belonging to the high risk group having a B:T cell ratio lower than 1:5. None of the six patients of the low risk group with a B:T cell ratio higher than 1:5 showed neurological reactions. It is therefore hypothesized that the mentioned (pre-symptomatic) central nervous system (CNS) treatment reduced the risk of a neurological reaction in the ALL patient in that the B lymphocytic target cells have been removed from the PVS and CNS, including the brain. However, in the absence of B target cells in these tissues, there is no full activation of the cytotoxic T cells. Therefore, less frequent neurological reactions could be observed in said patient populations.

Accordingly, the absence of one of the above factors, in the mentioned case the presence of target B cells in the PVS/CNS, could possibly help to prevent neurological reactions. However, for example, intrathecal chemotherapy is not the therapy of choice in NHL treatment. For instance, it is not effective in indolent NHL therapy, and it is not yet known whether it could be a treatment option for aggressive NHL. In addition, intrathecal chemotherapy is highly toxic for ALL patients and therefore associated with considerable health risks.

In light of the above, the depletion of any one of the above indicated factors without loosing therapeutic efficacy is no trivial task since it is for example not easily possible to avoid the presence of B cells in the PVS/CNS of NHL. Furthermore, it has also been found that other measures, including the pre- or co-administration of high doses of steroids could not prevent neurological reactions in the high risk patients.

However, by way of applying the methods/dosage regimens of the present invention, it is possible to ameliorate and/or prevent adverse effects for patients who are at an increased risk of such adverse effects if they have a B:T cell ratio of about 1:5 or lower. The present invention envisages providing dosage regimens (methods) which are even independent of the above mentioned factors that could influence a treatment with a CD19×CD3 bispecific antibody.

Thus, the present invention in a preferred aspect relates to a method for assessing (analyzing) the risk of potential adverse effects for a human patient mediated by the administration of a CD19×CD3 bispecific antibody to said patient comprising determining the ratio of B cells to T cells determining in a sample from said patient, wherein a ratio of about 1:5 or lower is indicative for a risk of potential adverse effects for said patient, wherein said patient is (a) administered a first dose of said antibody for a first period of time; and is consecutively (b) administered a second dose of said antibody for a second period of time;

wherein said second dose exceeds said first dose; for
(i) treating malignant CD19 positive lymphocytes; and/or
(ii) for ameliorating and/or preventing an adverse effect mediated by the administration of a CD19×CD3 bispecific antibody.

Preferably, in this preferred aspect, the patient is administered a third dose of said antibody for a third period of time as described in herein below. Accordingly, the embodiments and aspects described herein in the context of the three-stage method (dose regimen) are applicable to this preferred aspect.

In one aspect of the methods of the present invention said second period of time exceeds said first period of time. The term "exceeds" means that the second period of time is at least one day longer than the first period of time.

Each of the methods (dosage regimens) of the present invention can be repeated, for example, for one, two, three, four, five, six, or more times and in any event as often as there is a beneficial effect for a patient in ameliorating and/or treating malignant CD19 positive lymphocytes, thereby treating lymphoma or leukemia. Dependent on the ratio of the B:T cell ratio of a patient, in accordance with the teaching of the present invention the practitioner can decide as to whether the patient has to be "adapted" to a further treatment with a CD19×CD3 bispecific antibody prior by applying the dosage regimens of the present invention (i.e., administering a low dose of a CD19×CD3 bispecific antibody prior to administering a higher dose in order to "adapt" the patient).

It must be understood that the dose or day ranges given herein are illustrated by increments of one, two, three, four or five. These ranges, however, in case of increments higher than one also encompass smaller increments, for example those exemplified by increments of one (10 to 30 includes for example 10, 11, 12, 13, 13 etc. up to 30), or still smaller increments, for example values after the decimal point.

In another aspect of the present invention, it is envisaged that said first period of time is at least 3 days long, whereby even longer periods of time of for example 8, 9, 10, 11, 12, 13 or 14 days are not excluded. "Longer" is thereby not limited to a (one) complete day as the lowest time unit, i.e. ½ days, or fully hours are also conceivable. It is however preferred that the smallest time unit is one full day.

Accordingly, said first period of time exceeds 3 days. More preferably, it is envisaged that said first period of time is between 3 days and 10 days, with 7 days being particularly preferred.

As used herein, a time interval which is defined as "X to Y" equates with a time interval which is defined as "between X and Y". Both time intervals specifically include the upper limit and also the lower limit. This means that for example a time interval "3 to 10 days" or between "3 to 10 days" includes a period of time of one, two, three, four, five, six, seven and/or eight days.

As mentioned herein, the inventors observed that "adapting" a human patient having a B:T cell ratio of about 1:5 or lower to the treatment with a CD19×CD3 bispecific antibody during a first period of time allows the treatment of the human patient with an increased second dose of the antibody for a second period of time, whereby adverse effects (in particular neurological reactions) can be better controlled, i.e., could be avoided or at least kept within an acceptable grade in accordance with the CTCAE.

However, for achieving this improvement it is required to "adapt" the human patient having a B:T cell ratio of about 1:5 or lower to the CD19×CD3 bispecific antibody by administering a first dose of the antibody for a first period of time (wherein said first dose is lower than the consecutive (second) dose). The administration can be a bolus injection or a continuous administration, whereby a continuous administration is preferred.

Likewise the duration of the first period of time, the duration of the second period of time may be variable in view of, for example, the age, sex, body weight, etc. of the human patient.

Accordingly, in another aspect of the present invention, it is envisaged that said second period of time is at least 18 days long, whereby even longer periods of time of for example 19, 20, 25, 30, 35, 40, 45, 49, 50, 55, 60, 65, 60, 65, 70, 75, 80, 81, 82, 83, 84, 85, 86, 87, 88 or 90 days are not excluded. "Longer" is thereby not limited to a (one) complete day as the lowest time unit, i.e. ½ days, or fully hours are also conceivable. It is however preferred that the smallest time unit is one full day.

Accordingly, said second period of time exceeds 18 days. More preferably, it is envisaged that said second period of time is between 18 days and 81 days, with 21 or 49 days being particularly preferred.

As used herein, a time interval which is defined as "X to Y" equates with a time interval which is defined as "between X and Y". Both time intervals specifically include the upper limit and also the lower limit. This means that for example a time interval "18 to 81 days" or between "18 to 81 days" includes a period of time of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 34, 36, 38, 40, 42, 44, 46, 48, 50, 52, 54, 56, 58, 60, 61, 62, 63 and/or 64 days.

In a more preferred embodiment of the methods/dosage regimens of the present invention, said first period of time is between 3 days and 10 days, and said second period of time is between 18 and 81 days.

In an even more preferred embodiment, said first period of time is 7 days and said second period of time is 21 or 49 days.

In the clinical trials mentioned herein, it was observed that a dose of 15 $\mu g/m^2/d$ in the treatment of NHL effected tumor shrinkage as could be visualized in computer tomography. It was also observed that a dose of 15 $\mu g/m^2/d$ in the treatment of ALL resulted in minimal residual disease and could even eliminate MRD.

Minimal residual disease (MRD) is the name given, to small numbers of leukemic/lymphoma cells that remain in the patient during treatment or after treatment when the patient is in remission (no symptoms or signs of disease). Up until a decade ago none of the tests used to assess/detect cancer, were sensitive enough to detect MRD. Now, however, very sensitive molecular biology tests are available—based on DNA, RNA or Proteins—and these can measure minute levels of cancer cells in tissue samples, sometimes as low as 1 cancer cell in million normal cells.

In cancer treatment, particularly leukaemia, MRD testing has several important roles: determining whether treatment has eradicated the cancer or whether traces remain, comparing the efficacy of different treatments, monitoring patient remission status and recurrence of the leukemia or cancer and choosing the treatment that will best meet those needs (personalization of treatment)

Accordingly, in a further aspect of the methods/dosage regimens of the present invention, said first dose is between 1 and 15 $\mu g/m^2/d$, i.e. 1, 2, 3, 4, 5, 6, 7, 8, 9, 10, 11, 12, 13, 14, 15 $\mu g/m^2/d$. Particularly preferred is a dose of 5 or 15 $\mu g/m^2/d$.

As used herein, a dose interval which is defined as "between X and Y" equates with a dose interval which is defined as "X to Y". Both dose intervals specifically include the upper limit and also the lower limit. This means that for example a dose interval "between 1 and 15" or "1 to 15" includes a dose of 1, 2, 3, 4, 5, 6, 7, 8, 9, 10, 11, 12, 13, 14, 15 µg/m²/d.

"d" denotes one day.

"m²" denotes a square meter of a patient's body surface (BSA). The "normal" average BSA is generally taken to be about 1.73 m² for an adult, for a neonate it is about 0.25 m², for a 2 year old child it is about 0.5 m², for a 9 year old child it is about 1.07 m², for a 10 year old child it is about 1.14 m², for a 12-13 year old child it is about 1.33 m², for men it is about 1.9 m² and for women it is about 1.6 m².

However, the BSA can also be calculated more precisely by one of the following formulas (each of these formulas can be applied when calculating the BSA):

The Mosteller formula (Mosteller, N Engl J Med 1987 Oct. 22; 317(17): 1098):
BSA (m²)=([Height (cm)× Weight (kg)]/3600)$^{1/2}$ or in inches and pounds:
BSA (m²)=([Height (in)× Weight (lbs)]/3131)$^{1/2}$ The DuBois formula (DuBois, Arch Int Med 1916 17:863-871):
BSA (m²)=0.007184× Height (cm)$^{0.725}$× Weight (kg)$^{0.425}$ The Haycock formula (Haycock, The Journal of Pediatrics 1978 93:1: 62-66):
BSA (m²)=0.024265× Height (cm)$^{0.3964}$× Weight (kg)$^{0.5378}$ The Gehan formula (Gehan, Cancer Chemother Rep 1970 54:225-35):
BSA (m²)=0.0235× Height (cm)$^{0.42246}$× Weight (kg)$^{0.51456}$ The Boyd formula (Boyd, University of Minnesota Press, 1935)
BSA (m²)=0.0003207× Height (cm)$^{0.3}$× Weight (grams)$^{(0.7285-(0.0188 \times log\ 10(grams))}$ The term "µg" includes "µg of the CD19×CD3 bispecific antibody preparation". It is preferred that not more than 10% of said CD19×CD3 bispecific antibody preparation is incorrectly folded. It follows that in a preferred embodiment, 90%, 91%, 92%, 93%, 94%, 95%, 96%, 97%, 98%, 99% or even 100% of the CD19×CD3 bispecific antibody is correctly folded. It is also conceivable that the antibody preparation may optionally comprise further ingredients, for example a lyoprotectant, a surfactant, a filler, a binder, and/or bulking agent etc. The amount of such further ingredients is, preferably, not included in the term "µg" as used in the context of the "dose" and/or methods (dosage regimens) of the present invention.

A dose of, for example, 1 µg/m²/d means that 1 µg of the CD19×CD3 bispecific antibody is administered evenly or continuously across one day per square meter body surface. "Continuously across one day" refers to an infusion which is allowed to proceed permanently without interruption.

In a further aspect of the methods/dosage regimen of the present invention, said second dose is between 15 and 60 or 15 and 90 µg/m²/d, i.e. 15, 20, 25, 30, 35, 40, 45, 50, 55 and 60 µg/m²/d or 15, 20, 25, 30, 35, 40, 45, 50, 55, 60, 70, 80 and 90 µg/m²/d. Particularly preferred is a dose of 60 or 90 µg/m²/d. Said second dose is thus therapeutically active.

In a preferred embodiment, said first dose is between 5 and 15 µg/m²/d and said second dose is between 15 and 60 or 15 and 90 µg/m²/d.

As used herein, a dose interval which is defined as "between X and Y" equates with a dose interval which is defined as "X to Y". Both dose intervals specifically include the upper limit and also the lower limit. This means that for example a dose interval "between 15 and 60" or "15 to 60" includes a dose of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 and/or 60 µg/m²/d.

It must be understood that the ranges given herein are illustrated by increments of five. These ranges, however, also encompass smaller increments, for example those exemplified by increments of one (10 to 30 includes for example 10, 11, 12, 13, 13 etc. up to 30), or still smaller increments, for example values after the decimal point.

Preferably, not included in the methods for administering a CD19×CD3 bispecific antibody, for treating malignant CD19 positive lymphocytes, or for ameliorating and/or preventing an adverse effect mediated by the administration of a CD19×CD3 bispecific antibody are the following administration schemes:

(i) 5 µg/m² of the bispecific antibody for one day followed by administration of 15 µg/m² as daily dose for the remaining period (second and each further consecutive day); and/or (ii) 15 µg/m² of the bispecific antibody for one day followed by administration of 45 µg/m² as daily dose for the remaining period (second and each further consecutive day); and/or (iii) 5 µg/m² of the bispecific antibody for one day followed by administration of 15 µg/m² for one day, followed by administration of 45 µg/m² as daily dose for the remaining period (third and each further consecutive day); and/or (iv) less than 10-80 µg/m² of the bispecific antibody for one day followed by administration of a dose of 10-80 µg/m² (second and each further consecutive day); and/or (v) less than 10-80 µg/m² of the bispecific antibody for one day followed by administration of a dose of less 10-80 µg/m² for one day, followed by administration of a dose of less 10-80 µg/m² (third and each further consecutive day).

As mentioned herein, patients having a B:T cell ratio higher than 1:5, do not necessarily have to be adapted to the treatment with a CD19×CD3 bispecific antibody by way of the dosage regimen of the present invention. These patients having a decreased risk of potential adverse effects could be treated by administration of a CD19×CD3 bispecific antibody in a constant dose of 5 µg to 75 µg per square meter body surface area per day for at least four weeks. The administration is preferably a continuous administration.

In another embodiment of the methods (dosage regimen) of the present application, said methods further comprise administering after a first and second dose for a first and second period of time a third dose of said antibody for a third period of time. Accordingly, the present invention provides a three-stage method (dosage regimen).

The administration of said third dose is intravenously. It can be administered in the form of a bolus injection or continuously, with continuously being preferred.

In one aspect of the methods of the present invention said third period of time exceeds said first and second period of time. The term "exceeds" means that the third period of time is at least one day longer than the first and second period of time.

Likewise the duration of the first and second period of time, the duration of the third period of time may be variable in view of, for example, the age, sex, body weight, etc. of the human patient.

In the three-stage dosage regimen aspect of the present invention, it is envisaged that said first period of time is at least 3 days long, whereby even longer periods of time of for example 8, 9, 10, 11, 12, 13 or 14 days are not excluded. "Longer" is thereby not limited to a (one) complete day as the lowest time unit, i.e. ½ days, or fully hours are also conceivable. It is however preferred that the smallest time unit is one full day.

Accordingly, said first period of time exceeds 3 days. More preferably, it is envisaged that said first period of time is between 3 days and 10 days, with 7 days being particularly preferred.

As used herein, a time interval which is defined as "X to Y" equates with a time interval which is defined as "between X and Y". Both time intervals specifically include the upper limit and also the lower limit. This means that for example a time interval "3 to 10 days" or between "3 to 10 days" includes a period of time of one, two, three, four, five, six, seven and/or eight days.

In the three-stage dosage regimen aspect of the present invention, it is envisaged that said second period of time is at least 3 days long, whereby even longer periods of time of for example 8, 9, 10, 11, 12, 13 or 14 days are not excluded. "Longer" is thereby not limited to a (one) complete day as the lowest time unit, i.e. ½ days, or fully hours are also conceivable. It is however preferred that the smallest time unit is one full day.

Accordingly, said first period of time exceeds 3 days. More preferably, it is envisaged that said first period of time is between 3 days and 10 days, with 7 days being particularly preferred.

As used herein, a time interval which is defined as "X to Y" equates with a time interval which is defined as "between X and Y". Both time intervals specifically include the upper limit and also the lower limit. This means that for example a time interval "3 to 10 days" or between "3 to 10 days" includes a period of time of one, two, three, four, five, six, seven and/or eight days.

In the three-stage dosage regimen aspect of the present invention, it is envisaged that said third period of time is at least 8 days long, whereby even longer periods of time of for example 8, 9, 10, 11, 12, 13, 14, 15, 16, 17, 18, 19, 20, 21, 22, 23, 24, 25, 26, 27, 28, 29, 30, 32, 34, 36, 38, 40, 42, 44, 46, 48, 50, 52, 54, 56, 58, 60, 61, 62, 63, 64, 65, 66, 67, 68, 69, 70 and/or 71 days are not excluded. "Longer" is thereby not limited to a (one) complete day as the lowest time unit, i.e. ½ days, or fully hours are also conceivable. It is however preferred that the smallest time unit is one full day.

Accordingly, said first period of time exceeds 8 days. More preferably, it is envisaged that said first period of time is between 8 days and 78 days, with 14 or 42 days being particularly preferred.

As used herein, a time interval which is defined as "X to Y" equates with a time interval which is defined as "between X and Y". Both time intervals specifically include the upper limit and also the lower limit. This means that for example a time interval "18 to 78 days" or between "18 to 78 days" includes a period of time of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 34, 36, 38, 40, 42, 44, 46, 48, 50, 52, 54, 56, 58, 60, 61, 62 63, 64, 65, 66, 67, 68, 69, 70 and/or 71 days.

In a more preferred embodiment of the three-stage methods/dosage regimens of the present invention, said first period of time is between 3 days and 10 days, and said second period of time is between 3 days and 10 days, and said third period of time is between 8 days and 78 days.

In an even more preferred embodiment, said first period of time is 7 days, said second period of time is 7 days, and said third period of time is 14 or 42 days.

In an embodiment of the three-stage methods/dosage regimens of the present invention, said third dose exceeds said first and second dose. Said second and third dose are preferably therapeutically active. Of note, said second dose exceeds said first dose.

Accordingly, in a further aspect of the three-stage methods/dosage regimens of the present invention, said first dose is between 1 and 15 $\mu g/m^2/d$, preferably between 5 and 15 $\mu g/m^2/d$, i.e. 1, 2, 3, 4, 5, 6, 7, 8, 9, 10, 11, 12, 13, 14, 15 $\mu g/m^2/d$. Particularly preferred is a dose of 5 or 10 $\mu g/m^2/d$.

In a further aspect of the three-stage methods/dosage regimens of the present invention, said second dose is between 1 and 15 $\mu g/m^2/d$, preferably between 5 and 15 $\mu g/m2/d$, i.e. 1, 2, 3, 4, 5, 6, 7, 8, 9, 10, 11, 12, 13, 14, 15 $\mu g/m^2/d$. Particularly preferred is a dose of 15 $\mu g/m^2/d$.

As used herein, a dose interval which is defined as "between X and Y" equates with a dose interval which is defined as "X to Y". Both dose intervals specifically include the upper limit and also the lower limit. This means that for example a dose interval "between 1 and 15" or "1 to 15" includes a dose of 1, 2, 3, 4, 5, 6, 7, 8, 9, 10, 11, 12, 13, 14, 15 $\mu g/m^2/d$.

In a further aspect of the three-stage methods/dosage regimen of the present invention, said third dose is between 15 and 60 $\mu g/m^2/d$, more preferably between 20 and 60 $\mu g/m^2/d$, i.e. 15, 20, 25, 30, 35, 40, 45, 50, 55 and 60 $\mu g/m^2/d$. Particularly preferred is a dose of 60 $\mu g/m^2/d$. Alternatively, said third dose is between 15 and 90 $\mu g/m^2/d$, more preferably between 60 and 90 $\mu g/m^2/d$, i.e., 15, 20, 25, 30, 35, 40, 45, 50, 55, 60, 70, 80 and 90 $\mu g/m^2/d$.

In a preferred embodiment of the three-stage methods/dosage regimen of the present invention, said first dose is between 1 and 15 $\mu g/m^2/d$, said second dose is between 1 and 15 $\mu g/m^2/d$, and said third dose is between 15 and 60 or 15 and 90 $\mu g/m^2/d$.

Particularly preferred, said first dose is 5 $\mu g/m^2/d$, said second dose is 15 $\mu g/m^2/d$, and said third dose is 60 $\mu g/m^2/d$. Alternatively, said third dose may be 90 $\mu g/m^2/d$.

As used herein, a dose interval which is defined as "between X and Y" equates with a dose interval which is defined as "X to Y". Both dose intervals specifically include the upper limit and also the lower limit. This means that for example a dose interval "between 15 and 60" or "15 to 60" includes a dose of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 and/or 60 $\mu g/m^2/d$. Similarly, this means that for example a dose interval "between 15 and 90" or "15 to 90" includes a dose of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 86, 87, 88, 89 or 90 $\mu g/m^2/d$.

In view of the observations made by the present inventors that a three-stage (step) method/dosage regimen aids in avoiding adverse effects as described herein, the present invention relates to a method of treating malignant CD19 positive lymphocytes in a human patient, said method comprising (a) administering a first dose of said antibody for a first period of time; (b) administering a second dose of said antibody for a second period of time; and consecutively (c) administering a third dose of said antibody for a third period of time.

Also, the present invention relates to a method for treating malignant CD19 positive lymphocytes in a human patient, said method comprising (a) administering a first dose of said antibody for a first period of time; (b) administering a second dose of said antibody for a second period of time; and consecutively (c) administering a third dose of said antibody for a third period of time.

Furthermore, the present invention relates to a method for ameliorating and/or preventing an adverse effect mediated by the administration of a CD19×CD3 bispecific antibody to a human patient, said method comprising (a) administering a first dose of said antibody for a first period of time; (b) administering a second dose of said antibody for a second period of time; and consecutively (c) administering a third dose of said antibody for a third period of time.

Preferably, the first, second and third period of time are as described elsewhere herein.

Regarding the doses, it is preferred that the second dose exceeds the first dose and the third dose exceeds the second dose as described elsewhere herein. More preferably, the first dose is 5 μg/m²/d, the second dose is 15 μg/m²/d and the third dose is 60 μg/m²/d. Alternatively, the third dose may also be 90 or 120 μg/m²/d.

As noted herein above, the present invention relates to methods of treatment/dosage regimen which employ CD19×CD3 bispecific antibodies, comprising a first binding domain capable of binding to an epitope of human CD3 epsilon chain and a second binding domain capable of binding to human CD19. Examples for bispecific molecules according to the methods of the invention are described in great detail in WO 99/54440 and WO 2004/106381 and WO 2008/119565. All the specific CD19×CD3 bispecific antibodies disclosed therein, including their variants, fragments, equivalents etc. are particularly preferred CD19×CD3 bispecific antibodies of the present invention.

As used herein, a "CD19×CD3 bispecific antibody" (including a CD19×CD3 bispecific single chain antibody) denotes a single polypeptide chain comprising two binding domains. Such single chain antibodies are preferred in the context of the methods/dosage regimen of the present invention. Each binding domain comprises at least one variable region from an antibody heavy chain ("VH or H region"), wherein the VH region of the first binding domain specifically binds to the CD3 epsilon molecule, and the VH region of the second binding domain specifically binds to CD19. The two binding domains are optionally linked to one another by a short polypeptide spacer. A non-limiting example for a polypeptide spacer is Gly-Gly-Gly-Gly-Ser (G-G-G-G-S) (SEQ ID NO: 23) and repeats thereof. Each binding domain may additionally comprise one variable region from an antibody light chain ("VL or L region"), the VH region and VL region within each of the first and second binding domains being linked to one another via a polypeptide linker, for example of the type disclosed and claimed in EP 623679 B1, but in any case long enough to allow the VH region and VL region of the first binding domain and the VH region and VL region of the second binding domain to pair with one another such that, together, they are able to specifically bind to the respective first and second binding domains. Such CD19CD3 bispecific single chain antibodies are described in great detail in WO 99/54440 and WO 2004/106381.

The term "binding domain" characterizes in connection with the present invention a domain of a polypeptide which specifically binds to/interacts with a given target structure/antigen/epitope. Thus, the binding domain is an "antigen-interaction-site". The term "antigen-interaction-site" defines, in accordance with the present invention, a motif of a polypeptide, which is able to specifically interact with a specific antigen or a specific group of antigens, e.g. the identical antigen in different species. Said binding/interaction is also understood to define a "specific recognition". The term "specifically recognizing" means in accordance with this invention that the antibody molecule is capable of specifically interacting with and/or binding to at least two, preferably at least three, more preferably at least four amino acids of an antigen, e.g. the human CD3 antigen as defined herein. Such binding may be exemplified by the specificity of a "lock-and-key-principle". Thus, specific motifs in the amino acid sequence of the binding domain and the antigen bind to each other as a result of their primary, secondary or tertiary structure as well as the result of secondary modifications of said structure. The specific interaction of the antigen-interaction-site with its specific antigen may result as well in a simple binding of said site to the antigen. Moreover, the specific interaction of the binding domain/antigen-interaction-site with its specific antigen may alternatively result in the initiation of a signal, e.g. due to the induction of a change of the conformation of the antigen, an oligomerization of the antigen, etc. A preferred example of a binding domain in line with the present invention is an antibody. The binding domain may be a monoclonal or polyclonal antibody or derived from a monoclonal or polyclonal antibody.

The term "antibody" comprises derivatives or functional fragments thereof which still retain the binding specificity. Techniques for the production of antibodies are well known in the art and described, e.g. in Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1999. The term "antibody" also comprises immunoglobulins (Ig's) of different classes (i.e. IgA, IgG, IgM, IgD and IgE) and subclasses (such as IgG1, IgG2 etc.).

The definition of the term "antibody" also includes embodiments such as chimeric, single chain and humanized antibodies, as well as antibody fragments, like, inter alia, Fab fragments. Antibody fragments or derivatives further comprise F(ab')2, Fv, scFv fragments or single domain antibodies, single variable domain antibodies or immunoglobulin single variable domain comprising merely one variable domain, which might be VH or VL, that specifically bind to an antigen or epitope independently of other V regions or domains; see, for example, Harlow and Lane (1988) and (1999), cited above. Such immunoglobulin single variable domain encompasses not only an isolated antibody single variable domain polypeptide, but also larger polypeptides that comprise one or more monomers of an antibody single variable domain polypeptide sequence.

As used herein, CD3 epsilon denotes a molecule expressed as part of the T cell receptor and has the meaning as typically ascribed to it in the prior art. In human, it encompasses in individual or independently combined form all known CD3 subunits, for example CD3 epsilon, CD3 delta, CD3 gamma, CD3 zeta, CD3 alpha and CD3 beta. The human CD3 epsilon is indicated in GenBank Accession No. NM_000733.

The human CD19 protein is indicated in GenBank Accession No. AAA69966.

Preferably, the bispecific antibody applied in the methods/dosage regimens of the present invention has the domain arrangement VL(CD19)-VH(CD19)-VH(CD3)-VL(CD3).

It is, however, also envisaged that the methods of the invention can be carried out with CD19×CD3 bispecific single chain antibodies of other domain arrangements, such as
VH(CD19)-VL(CD19)-VH(CD3)-VL(CD3),
VL(CD19)-VH(CD19)-VL(CD3)-VH(CD3),
VH(CD19)-VL(CD19)-VL(CD3)-VH(CD3),
VL(CD3)-VH(CD3)-VH(CD19)-VL(CD19),
VH(CD3)-VL(CD3)-VH(CD19)-VL(CD19),
VL(CD3)-VH(CD3)-VL(CD19)-VH(CD19), or
VH(CD3)-VL(CD3)-VL(CD19)-VH(CD19).

A preferred CD19×CD3 bispecific antibody applied in the methods of the present invention comprises the
- (a) anti-CD3 CDRs of the heavy chain shown as CD3 CDR-H1 in SEQ ID NO: 24 (RYTMH), more preferably in SEQ ID NO: 11 (GYTFTRYTMH), CD3 CDR-H2 in SEQ ID NO: 12 (YINPSRGYTNYNQKFKD) and CD3 CDR-H3 in SEQ ID NO: 13 (YYDDHYCLDY); and/or
- (b) anti-CD3 CDRs of the light chain shown as CD3 CDR-L1 in SEQ ID NO: 14 (RASSSVSYMN), CD3 CDR-L2 in SEQ ID NO: 15 (DTSKVAS) and CD3 CDR-L3 in SEQ ID NO: 16 (QQWSSNPLT); and/or
- (c) anti-CD19 CDRs of the heavy chain shown as CD19 CDR-H1 in SEQ ID NO: 25 (SYWMN), more preferably in SEQ ID NO: 17 (GYAFSSYWMN), CD19 CDR-H2 in SEQ ID NO: 18 (QIWPGDGDTNYNGKFKG) and CD19 CDR-H3 in SEQ ID NO: 19 (RETTTVGRYYYAMDY); and/or
- (d) anti-CD19 CDRs of the light chain shown as CD19 CDR-L1 in SEQ ID NO: 20 (KASQSVDYDGDSYLN), CD19 CDR-L2 in SEQ ID NO: 21 (DASNLVS) and CD19 CDR-L3 in SEQ ID NO: 22 (QQSTEDPWT).

It is more preferred that the CD19×CD3 bispecific antibody applied in the methods of the present invention comprises the CD3 CDRs of the heavy and light chain. Even more preferably, the CD19×CD3 bispecific antibody applied in the methods of the present invention comprises the CD3 CDRs of the heavy and light chain as well as the CD19 CDRs of the heavy and light chain.

The CDRs referred to herein are in accordance with the Kabat numbering system. The Kabat numbering scheme is a widely adopted standard for numbering the residues in an antibody in a consistent manner (Kabat et al., Sequences of Proteins of Immunological Interest, 1991).

Alternatively, it is preferred that the CD19×CD3 bispecific antibody applied in the methods of the present invention comprises the
- (a) CD19 variable heavy chain shown in SEQ ID NO: 3 (nucleotide sequence is shown in SEQ ID NO: 4); and/or
- (b) CD19 variable light chain shown in SEQ ID NO: 5 (nucleotide sequence is shown in SEQ ID NO: 6); and/or
- (c) CD3 variable heavy chain shown in SEQ ID NO: 7 (nucleotide sequence is shown in SEQ ID NO: 8); and/or
- (d) CD3 variable light chain shown in SEQ ID NO: 9 (nucleotide sequence is shown in SEQ ID NO: 10).

More preferably, the CD19×CD3 bispecific antibody applied in the methods of the present invention comprises the CD19 variable heavy and light chain and/or the CD3 variable heavy and light chain. Even more preferably, the CD19×CD3 bispecific antibody applied in the methods of the present invention comprises the CD19 variable heavy and light chain as well as the CD3 variable heavy and light chain.

In another alternative, it is also preferred that said bispecific single chain antibody comprises an amino acid sequence selected from the group consisting of
- (a) an amino acid sequence as depicted in SEQ ID NO: 1;
- (b) an amino acid sequence encoded by a nucleic acid sequence as shown in SEQ ID NO: 2;
- (c) an amino acid sequence encoded by a nucleic acid sequence having at least 70%, 80%, 90%, 95% or 99% identity to a nucleic acid sequence of (b), wherein said amino acid sequence is capable of specifically binding to CD3 and CD19; and
- (d) an amino acid sequence encoded by a nucleic acid sequence which is degenerate as a result of the genetic code to a nucleotide sequence of (b), wherein said amino acid sequence is capable of specifically binding to CD3 and CD19.

It is to be understood that the sequence identity is determined over the entire amino acid sequence. For sequence alignments, for example, the programs Gap or BestFit can be used (Needleman and Wunsch J. Mol. Biol. 48 (1970), 443-453; Smith and Waterman, Adv. Appl. Math 2 (1981), 482-489), which is contained in the GCG software package (Genetics Computer Group, 575 Science Drive, Madison, Wis., USA 53711 (1991). It is a routine method for those skilled in the art to determine and identify an amino acid sequence having e.g. 70%, 80%, 90%, 95%, 96%, 97%, 98% or 99% sequence identity to the amino acid sequences of the CD19×CD3 bispecific antibody described herein (preferably MT103). For example, according to Crick's Wobble hypothesis, the 5' base on the anti-codon is not as spatially confined as the other two bases, and could thus have non-standard base pairing. Put in other words: the third position in a codon triplet may vary so that two triplets which differ in this third position may encode the same amino acid residue. Said hypothesis is well known to the person skilled in the art (see e.g. http colon-backslash-backslash en.wikipedia.org/wiki/Wobble_Hypothesis; Crick, J Mol Biol 19 (1966): 548-55). It is furthermore a routine procedure for those skilled in the art to determine cytotoxic activity of such an amino acid sequence having e.g. 70%, 80%, 90%, 95%, 96%, 97%, 98% or 99% sequence identity to the nucleotide or amino acid sequences of the CD19×CD3 bispecific single chain antibody described herein. Cytotoxic activity of the CD19×CD3 bispecific single chain antibody or an antibody construct having e.g. 70%, 80%, 90%, 95%, 96%, 97%, 98% or 99% sequence identity to the amino acid sequences of the CD19×CD3 bispecific single chain antibody can be determined by methods as illustrated e.g. in WO 99/54440.

Particularly preferred, said CD19×CD3 bispecific single chain antibody has the amino acid sequence shown in SEQ ID NO: 1.

Also particularly preferred is the CD19×CD3 bispecific antibody MT103 described in WO 99/54440 as well as those CD19×CD3 bispecific antibodies described in WO 2004/106381 and WO 2008/119565.

The present invention furthermore relates to a CD19×CD3 bispecific antibody for:
- (i) administering a CD19×CD3 bispecific antibody to a human patient, or
- (ii) treating malignant CD19 positive lymphocytes in a human patient; or
- (iii) ameliorating or preventing an adverse effect mediated by the administration of a CD19×CD3 bispecific antibody to a human patient;

wherein said antibody is to be administered in accordance with a dosage regimen as defined in any one of the preceding claims.

Also, the present invention relates to a CD19×CD3 bispecific antibody
(i) administering a CD19×CD3 bispecific antibody to a human patient, or
(ii) treating malignant CD19 positive lymphocytes in a human patient; or
(iii) ameliorating or preventing an adverse effect mediated by the administration of a CD19×CD3 bispecific antibody to a human patient;
wherein said antibody is to be administered in accordance with a method as defined in any one of the preceding claims.

In a further aspect, the present invention concerns the use of a CD19×CD3 bispecific antibody for the preparation of a pharmaceutical composition to be used in a method as defined in any one of the preceding claims.

The pharmaceutical composition of the present invention may optionally comprise a pharmaceutical carrier. Examples of suitable pharmaceutical carriers are well known in the art and include phosphate buffered saline solutions, sterile solutions etc. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents such as chemotherapeutic agents as explained herein elsewhere.

In a further aspect, the present invention relates to a (pharmaceutical) kit or pharmaceutical package comprising the first dose and the second dose as defined herein.

In another embodiment, the present invention relates to a (pharmaceutical) kit or pharmaceutical package comprising the first dose and the second dose as defined herein as well as the third dose as defined in the context of the three-stage dosage regimen/method.

In another aspect, the (pharmaceutical) kit or pharmaceutical package comprises all three doses as defined herein in the context of the three-stage dosage regimen/method, i.e., the first, the second and the third dose.

Said first, second and third dose are thereby packaged together in one sealed pharmaceutical package or kit. It will be understood that the "first dose", the "second dose" and the "third dose" encompasses in this regard the respective number of single doses which will be used for a given period of time (either the first or the second period of time). This means for example that the "first dose" or "second dose" which is comprised in the pharmaceutical package or kit of the present invention comprises, for example, 7 daily doses which are separated. The number of packaged daily doses thereby reflects the intended period of time (X daily doses if said period of time is X days, Y daily doses if the period of time is Y days and so on). In these embodiments, the (pharmaceutical) kit or pharmaceutical package comprises the daily dosages in separate containers, in a single package.

Alternatively, it is also envisaged that the intended first dose and/or second dose and/or third dose is not separated into the respective number of daily doses but is contained, either in toto or in part, in one single container (for example an infusion bag), which comprises the required dose for either the first and/or the second period of time either in part (for example for 1 to 3 days) or in toto (i.e. for the first or second period of time). This means that one single container comprises for example 7 daily doses for the "first dose" which is to be used during the first period of time etc.

It will be understood that the (pharmaceutical) kit or pharmaceutical package of the present invention may also comprises more or less daily doses as required for the respective period of time (either separated or not). Alternatively, the (pharmaceutical) kit or pharmaceutical package is prepared such that it contains the required number of daily doses (either separated or not) for the first and second period of time as defined herein, i.e. the "first dose", the "second dose" and the "third dose" in one single package. Such a package is ideally sufficient for one complete treatment of a patient (including the first and the second period of time). Parts of the kit and package of the invention can be packaged individually in vials or bottles or in combination in containers or multicontainer units. The manufacture of the kits follows preferably standard procedures which are known to the person skilled in the art.

Furthermore, the invention relates to a pharmaceutical package or kit as described hereinbefore and written instructions for the sequential use thereof in accordance with the methods of the present invention. Said pharmaceutical package or kit may further comprise a label or imprint indicating that the contents can be used for treating malignant CD19 positive lymphocytes present in lymphoma or leukemia in a human patient; or for ameliorating or preventing an adverse effect mediated by the administration of a CD19×CD3 bispecific antibody to a patient.

It is also envisaged that the pharmaceutical package or kit of the present invention, further comprises means to administer the first and/or the second dose and/or third dose to a patient and/or buffers, vials, teflon bags or infusion bags which are normally used for the infusion of therapeutic agents. "Means" thereby includes one or more article(s) selected from the group consisting of a syringe, a hypodermic needle, a cannula, a catheter, an infusion bag for intravenous administration, intravenous vehicles, vials, buffers, stabilizers, written instructions which aid the skilled person in the preparation of the respective doses and infusions of the invention etc.

It is also envisaged that the pharmaceutical package or kit of the present invention further comprises a chemotherapeutic agent.

In a further aspect, the present invention provides for a pharmaceutical package or kit, wherein said first and/or said second dose is arranged such, that it is suitable for (prepared for) administration of a dosage regimen in accordance with a method of any one of the preceding claims.

EXAMPLES

The following examples illustrate the invention. These examples should not be construed as to limit the scope of this invention. The examples are included for purposes of illustration and the present invention is limited only by the claims.

Example 1

Identification of a Predictive Factor for Reversible Neurological Adverse Events in a Subset of Non-Hodgkin Lymphoma Patients Treated with CD19-Specific BiTE Antibody Blinatumomab Blinatumomab is a CD19/CD3-bispecific antibody construct of the bispecific T cell engager (BiTE®) class showing as single agent a high rate and duration of responses in patients with relapsed non-Hodgkin lymphoma (NHL) and B-precursor acute lymphocytic leukemia (ALL). Blinatumomab has a favorable safety profile with exception of a subset of patients developing neurological adverse events (AEs) during the first days of treatment, such as confusion, speech impairment or cerebellar symptoms. Thus far, all relevant neurological AEs (11 out of 48 patients) were transient, fully reversible and resolved without sequelae within 3 to 72 hours after stop of infusion. In no case, pathological findings were seen upon cranial magnetic resonance imaging. Despite treatment discontinuation, 4 patients with neurological AEs have achieved an objective lymphoma remission. Analysis of cerebrospinal fluid (CSF) taken within hours after stop of infusion showed detectable levels of blinatumomab in the majority of affected patients, while in one patient without neurological symptoms no blinatumomab was detectable in CSF during infusion. Moreover, increased levels of albumin and T lymphocytes in CSF support a disturbance of the blood brain barrier (BBB) as a possible underlying event. Analyses of patient serum samples for angiopoetin-2 and S1008 are ongoing to investigate whether levels of the endothelial stress and BBB integrity marker, respectively, correlate with neurological AEs. In a retrospective analysis of 39 NHL patients, a baseline B cell to T cell (B:T) ratio in peripheral blood at or below 1:10 was identified as the only predictive factor for the subsequent occurrence of neurological AEs. The predictive value was then prospectively confirmed in 8 additional patients. Of note, ALL patients—despite very low B:T ratios—rarely showed neurological AEs, which may relate to previous intrathecal chemotherapy depleting target cells in the brain. Potential mechanisms for the neuroprotective effect of peripheral B cells are being investigated. In conclusion, we identified a simple measure to prospectively identify patients at risk of developing neurological AEs after onset of blinatumomab treatment. Mitigating measures are currently tested in these high-risk patients in order to avoid discontinuation of treatment.

Example 2

Synopsis of Observations (1) in Patients Treated with a CD19×CD3 Bispecific Antibody
  Synopsis of Observations (1)
  Common Features of Early CNS Events
    First symptoms appear 12-48 h after start of MT103 infusion: Agitation, speech impairment, sometimes tremor, ataxia
    More severe symptoms leading to infusion stop appear after 24-72 h: Confusion, disorientation, ataxia, aphasia, seizure
    After stop of MT103 infusion, complete resolution of CNS symptoms seen within 1-3 days; generally no sequelae
    Most CNS events fall into early activation and redistribution phase of polyclonal T cells
  Features of CNS Events with Slow Onset
    Biased to cerebellar symptoms
    Occur at various time points during treatment, frequently at beginning of treatment or at step Increase
    Tremor, mild speech impairment, mild writing impairment; can last for several days
  Other CNS Events
    Additional symptoms observed without proven relationship to other CNS events: Headache, fever, nausea
  MT103 Dose Response Relationship of CNS Events
    Dose response relationship of CNS events is evident; cut off is between dose level of 5 and 15 $\mu g/m^2/d$ Example 3

Synopsis of Observations (2) in Patients Treated with a CD19×CD3 Bispecific Antibody
  Synopsis of Observations (2)
  CNS Events Appear to be Predictable
    Correlation of CNS events with low B:T cell ratio (or low B cell count)
    B:T ratio of <1:10 identified as apparent cut off for development of CNS events
    No other biochemical or clinical parameters appear to correlate with CNS events
  Cranial MRI of Patients with CNS Events Mostly without Pathological Findings CSF Analyses Suggest Opening of BBB and Neuroinflammatory Event
    Detectable levels of MT103 and increased levels of protein and serum albumin found in majority of affected patients suggest temporary breakdown of blood brain barrier (BBB)
    No MT103 found in CSF of one patient free of CNS events
    CSF analysis also shows in some affected patients increased counts of monocytes and T lymphocytes indicative of neuroinflammatory process
    Are CNS events reflecting gradual opening of BBB (agitation>confusion>aphasia, ataxia>seizure)?
  Incidence of CNS Events May Correlate with Disease and/or Tumor Load
    At 15 $\mu g/m^2/d$, 3/8 NHL patients (37%) and only one of 1/11 ALL 'high risk' patients (9%) developed CNS events
    B-ALL patients routinely receive intrathecal chemotherapy (and i.v. high-dose methotrexate) likely reducing tumor cell load in CNS ("occult meningeosis neoplastica")

Example 4

Summary of CNS Events in Patients Treated with a CD19×CD3 Bispecific Antibody

Summary of Clinically Relevant CNS Events in NHL Patients

| Patient # | Neurological Assessment | Disease | B:T cell ratio | Gender, Age | First or Additional Treatment | Dose in $\mu g/m^2/$ Day | Treatment Stop after Start | Complete Resolution, Time | Best Response |
|---|---|---|---|---|---|---|---|---|---|
| 105-005 | Confusion, communication disorder | FL | 1:23.9 | Female, 65 | First | 15 | 15 h | Yes, 24 h | SD |
| 102-004 | Organic Brain Syndrome | MCL | 1:757 | Male, 75 | First | 15 | 50 h | Yes, 34 h | n.d. |
| 102-006 | Generalized seizure (acidosis) | MZL | 1:1740 | Male, 59 | First | 30 | 48 h | Yes, 48 h | n.d. |
| 109-011 | Cerebellar Symptoms | MCL | 1:9:2 | Male, 73 | Restart | 60 | 48 h | Yes, 24 h | PR (first) |

-continued

Summary of Clinically Relevant CNS Events in NHL Patients

| Patient # | Neurological Assessment | Disease | B:T cell ratio | Gender, Age | First or Additional Treatment | Dose in µg/m²/Day | Treatment Stop after Start | Complete Resolution, Time | Best Response |
|---|---|---|---|---|---|---|---|---|---|
| 109-012 | Encephalopathy | MCL | 1:19520 | Male, 55 | Additional | 60 | 24 h | Yes, 24 h | CR (first) |
| 102-007 | Seizure, aphasia | FL | 1:197 | Male, 61 | First | 90 | 48 h | Yes, 48 h | ?PR? |
| 109-023 | Encephalopathy | MCL | 1:368 | Male, 60 | First | 60 | 17 h | Yes, 56 h | n.d. |
| 109-025 | Encephalopathy | MCL | 1:873 | Male, 58 | First | 15 | 41 h | Yes, 48 h | n.d. |
| 108-004 | Speech Impairment Palsy Face and Arm | FL | 0:431 | Male, 66 | First | 60 | 624 h | Yes, 3 h | PR |
| 109-261 | Desorientation, Speech Impairment | MCL | 1:20 | Male, 42 | Additional | 60 | 30 h | Yes, 72 h | PR (first cycle) |

Example 5

Dose Dependency of CNS Events of Patients Treated with a CD19×CD3 Bispecific Antibody in Clinical Trials Dose Dependency of CNS Events in Ongoing NHL Trial
'High risk' patients defined by having low B:T cell ratio (<1:10)
Initial dose considered for classification in dose groups

| Dose | All | 'High Risk' | 'Low Risk' |
|---|---|---|---|
| ≤5 | 0/14 (0%) | 0/4+ (0%) | 0/10 (0%) |
| 15 | 3/16 (19%) | 3/8+ (38%) | 0/8 (0%) |
| 30 | 1/6 (17%) | 1/1 (100%) | 0/5 (0%) |
| 60 | 5/13 (38%) | 4/5 (80%) | 1*/8 (13%) |
| 90 | 2/3 (66%) | 1/1 (100%) | 1/2 (50%) |
| All | 11/52§ (21%) | 9/19 (47%) | 2/33 (6%) |

§>48 patients is due to additional treatments and re-starts of individual patients (resulting in conversion to 'high risk')
*Reached borderline B:T ratio after first treatment cycle
+Incl. patients with step-wise dose increase Example 6

A Patient Having an Increased Risk of Potential Adverse Effects Who Received 15 µg/m²/d for 7 Days and 60 µg/m²/d for 21 Days Showed No Adverse Effects (Neurological Reactions)
  Patient 108-003
  Female, 66 y
  FL grade 2, IVB (FD: September 2006)
  Relevant medical history: anemia, thrombocytopenia, (pre-treatment 2× Zevalin and bone marrow infiltration by FL) elevation of gGT and AP, abuse of benzodiazepines, status after 2. aureaus sepsis with spondylodiscitis and abscesses
  Prior lymphoma treatment:
    6× R-CHOP 14, 8× R September 2006-February 2007
    R mono May 2007
    1. Zevalin November 2007
    2. Zevalin January 2008
  Patient 108-003
  According to initial B:T cell ratio (1:10.5) high-risk (cohort 15/60)
  Jan. 5, 2009 Treatment start (15 µg/m²/24 h)
  Fever, headache for 2 days—easily handled by oral paracetamol and novalgin
  January 12th dose increase to 60 µg/m²/24 h
  Again fever, headache—easily handled by oral paracetamol and novalgin
  No neurological events
  Well tolerated dose "step"
  Suspected improvement of bone marrow function Example 7

A Patient Having an Increased Risk of Potential Adverse Effects Who Received 5 µg/m²/d for 7 Days and 60 µg/m²/d for 21 Days Showed Mild Adverse Effects (Neurological Reactions)
  MCL, male 42 y
  B:T 1:12
  Treatment start Jan. 19, 2009 with 5 micg/m2/d
  Day 1: fever and chills, headache, no further problems
  Step: January 26th: after 6 h fever, strong headache
  27, Jan. 2009: tiredness, nausea, vomiting, endoscopy without pathological findings), absolute arrhythmia with frequency up to 170/min→resolution within one day after substitution of potassium and digitoxin.
  Cranial CT scan and CSF perfomed, CT: no pathological findings
  CSF: slightly elevated protein 55 mg/dL, cells: 23 Zellen/micL, mainly monocytic cells and some activated lymphocytes
  27, Jan. 2009 afternoon: mild tremor, apraxia, "slow mental state", evening: mild speech impairment (cerebellar?), slow improvement over the next two days 29, Jan. 2009 due to ongoing mild symptoms decision to give dexamethasone
  Slow improvement of symptoms, complete resolution 31, Mar. 2009
  During the further course of treatment: recurrent difficulties to play the guitar.
  After 4 weeks treatment: −37%
  After 8 weeks of treatment: PR/CRu Example 8

A Patient Having an Increased Risk of Potential Adverse Effects Who Received a Treatment Regimen According to the Present Invention.
  Patient 108-005
  Male, 71 y, FL IIIB
  13:T cell ratio: 57:1363 (low, 1:23.9)
  First diagnosis: 1997

Multiple prior treatments: 12× Rituximab (mono), 6× Rituximab-Bendamustin, 6× R-CHOP, autologous SCT
Date of Blinatumomab start: 17.8.2009
Treatment duration: 8 weeks
Well tolerated (no SAE)
No neurological adverse event
8 Week CT Scan: −65%=partial remission of the lymphoma Example 9

A Further Patient Having an Increased Risk of Potential Adverse Effects Who Received a Treatment Regimen According to the Present Invention.

Patient 109-031
Male, 60 y, Follicular Lymphoma IVAE
B:T cell ratio: 0:429 (low)
First diagnosis: May 2009
Prior treatments: Pre-phase w. Vincristin/Decortin, 6× R-CHOP
Blinatumomab treatment Start: 30, Nov. 2009
Treatment duration: 8 weeks
Well tolerated (flush symptoms at steps—responsive to steroids)
No neurological adverse event
Lymphoma −56% after 8 weeks (partial remission of the lymphoma)

The invention claimed is:

1. A method for treating B-lineage acute lymphoblastic leukemia (ALL) in a human patient, said method comprising:
   (a) determining the total B cell number and total T cell number in a peripheral blood sample of said patient;
   (b) calculating the B:T cell ratio from the total B cell number and the total T cell number in a peripheral blood sample of said patient; and
   (c) administering to the patient having a B:T cell ratio of 1:5 or lower a CD19×CD3 bispecific single chain antibody comprising two binding domains:
      (i) a CD19 binding domain comprising anti-CD19 heavy chain CDRs of CDR-H1 as set forth in SEQ ID NO: 17, CDR-H2 as set forth in SEQ ID NO: 18, and CDR-H3 as set forth in SEQ ID NO: 19, and anti-CD19 light chain CDRs of CDR-L1 as set forth in SEQ ID NO: 20, CDR-L2 as set forth in SEQ ID NO: 21 and CDR-L3 as set forth in SEQ ID NO: 22; and
      (ii) a CD3 binding domain comprising anti-CD3 heavy chain CDRs of CDR-H1 as set forth in SEQ ID NO: 11, CDR-H2 as set forth in SEQ ID NO: 12, and CDR-H3 as set forth in SEQ ID NO: 13; and anti-CD3 light chain CDRs of CDR-L1 as set forth in SEQ ID NO: 14, CDR-L2 as set forth in SEQ ID NO: 15, and CDR-L3 as set forth in SEQ ID NO: 16 in a step dose regimen, wherein in the step dose regimen a first dose of between 5 and 15 μg/m$^2$/d is administered for a first period of time of at least three days, a second dose of between 5 and 15 μg/m$^2$/d of said CD19×CD3 bispecific antibody is subsequently administered for a second period of time, wherein the second period of time exceeds the first period of time, and wherein the second dose exceeds the first dose, and a third dose of between 15 and 60 μg/m$^2$/d is administered for a third period of time.

2. The method of claim 1, wherein the route of administration is intravenous.

3. The method of claim 1, wherein said second period of time exceeds 18 days.

4. The method of claim 3, wherein said second period of time is between 18 days and 81 days.

5. The method of claim 1, wherein said second period of time exceeds 3 days.

6. The method of claim 1, wherein said second period of time is between 3 days and 10 days.

7. The method of claim 1, wherein said third period of time exceeds 8 days.

8. The method of claim 1, wherein said third period of time is between 8 days and 78 days.

9. The method of claim 1, wherein said antibody is administered at a first dose of 5 µg/m$^2$/d, followed by a second dose of 15 µg/m$^2$/d and consecutively followed by a third dose of 60 µg/m$^2$/d.

10. The method of claim 1, wherein the CD19×CD3 bispecific antibody comprises
    (a) the anti-CD19 variable heavy chain as set forth in SEQ ID NO: 3 and the anti-CD19 variable light chain as set forth in SEQ ID NO: 5; and
    (b) the anti-CD3 variable heavy chain as set forth in SEQ ID NO: 7 and the anti-CD3 variable light chain as set forth in SEQ ID NO: 9.

11. The method of claim 1, wherein the CD19×CD3 bispecific antibody comprises an amino acid sequence comprising at least 70% identity to the amino acid sequence as set forth in SEQ ID NO: 1.

12. The method of claim 11, wherein the CD19×CD3 bispecific antibody comprises the amino acid sequence as set forth in SEQ ID NO: 1.

13. The method of claim 1, wherein the CD19×CD3 bispecific antibody comprises an amino acid sequence comprising at least 80% identity to the amino acid sequence as set forth in SEQ ID NO: 1.

14. The method of claim 1, wherein the CD19×CD3 bispecific antibody comprises an amino acid sequence comprising at least 90% identity to the amino acid sequence as set forth in SEQ ID NO: 1.

15. The method of claim 1, wherein the CD19×CD3 bispecific antibody comprises an amino acid sequence comprising at least 95% identity to the amino acid sequence as set forth in SEQ ID NO: 1.

16. The method of claim 1, wherein the CD19×CD3 bispecific antibody comprises an amino acid sequence encoded by a nucleotide sequence comprising at least 70% identity to the nucleotide sequence as set forth in SEQ ID NO: 2.

17. The method of claim 1, wherein the CD19×CD3 bispecific antibody comprises an amino acid sequence encoded by a nucleotide sequence comprising at least 80% identity to the nucleotide sequence as set forth in SEQ ID NO: 2.

18. The method of claim 1, wherein the CD19×CD3 bispecific antibody comprises an amino acid sequence encoded by a nucleotide sequence comprising at least 90% identity to the nucleotide sequence as set forth in SEQ ID NO: 2.

19. The method of claim 1, wherein the CD19×CD3 bispecific antibody comprises an amino acid sequence encoded by a nucleotide sequence comprising at least 95% identity to the nucleotide sequence as set forth in SEQ ID NO: 2.

20. The method of claim 1, wherein the CD19×CD3 bispecific antibody comprises an amino acid sequence encoded by the nucleotide sequence as set forth in SEQ ID NO: 2.

* * * * *

SEQUENCE LISTING

```
<160> NUMBER OF SEQ ID NOS: 25

<210> SEQ ID NO 1
<211> LENGTH: 498
<212> TYPE: PRT
<213> ORGANISM: Artificial Sequence
<220> FEATURE:
<223> OTHER INFORMATION: CD19xCD3 bispecific single chain antibody

<400> SEQUENCE: 1

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
```

```
                          260                265                270
Val Lys Met Ser Cys Lys Thr Ser Gly Tyr Thr Phe Thr Arg Tyr Thr
                275                280                285
Met His Trp Val Lys Gln Arg Pro Gly Gln Gly Leu Glu Trp Ile Gly
            290                295                300
Tyr Ile Asn Pro Ser Arg Gly Tyr Thr Asn Tyr Asn Gln Lys Phe Lys
305                310                315                320
Asp Lys Ala Thr Leu Thr Thr Asp Lys Ser Ser Ser Thr Ala Tyr Met
                325                330                335
Gln Leu Ser Ser Leu Thr Ser Glu Asp Ser Ala Val Tyr Tyr Cys Ala
                340                345                350
Arg Tyr Tyr Asp Asp His Tyr Cys Leu Asp Tyr Trp Gly Gln Gly Thr
                355                360                365
Thr Leu Thr Val Ser Ser Val Glu Gly Gly Ser Gly Gly Ser Gly Gly
            370                375                380
Ser Gly Gly Ser Gly Gly Val Asp Asp Ile Gln Leu Thr Gln Ser Pro
385                390                395                400
Ala Ile Met Ser Ala Ser Pro Gly Glu Lys Val Thr Met Thr Cys Arg
                405                410                415
Ala Ser Ser Ser Val Ser Tyr Met Asn Trp Tyr Gln Gln Lys Ser Gly
                420                425                430
Thr Ser Pro Lys Arg Trp Ile Tyr Asp Thr Ser Lys Val Ala Ser Gly
            435                440                445
Val Pro Tyr Arg Phe Ser Gly Ser Gly Ser Gly Thr Ser Tyr Ser Leu
450                455                460
Thr Ile Ser Ser Met Glu Ala Glu Asp Ala Ala Thr Tyr Tyr Cys Gln
465                470                475                480
Gln Trp Ser Ser Asn Pro Leu Thr Phe Gly Ala Gly Thr Lys Leu Glu
                485                490                495
Leu Lys

<210> SEQ ID NO 2
<211> LENGTH: 1494
<212> TYPE: DNA
<213> ORGANISM: Artificial Sequence
<220> FEATURE:
<223> OTHER INFORMATION: CD19xCD3 bispecific single chain antibody

<400> SEQUENCE: 2
gatatccagc tgacccagtc tccagcttct ttggctgtgt ctctagggca gagggccacc      60
atctcctgca aggccagcca agtgttgat tatgatggtg atagttattt gaactggtac      120
caacagattc caggacagcc acccaaactc ctcatctatg atgcatccaa tctagtttct      180
gggatcccac ccaggtttag tggcagtggg tctgggacag acttcaccct caacatccat      240
cctgtggaga aggtggatgc tgcaacctat cactgtcagc aaagtactga ggatccgtgg      300
acgttcggtg gagggaccaa gctcgagatc aaaggtggtg tggttctgg cggcggcggc      360 tccggtggtg gtggttctca ggtgcagctg cagcagtctg ggctgagct ggtgaggcct      420 gggtcctcag tgaagatttc ctgcaaggct tctggctatg cattcagtag ctactggatg      480
aactgggtga agcagaggcc tggacagggt cttgagtgga ttggacagat ttggcctgga      540
gatggtgata ctaactacaa tggaaagttc aagggtaaag ccactctgac tgcagacgaa      600
tcctccagca cagcctacat gcaactcagc agcctagcat ctgaggactc tgcggtctat      660
ttctgtgcaa gacgggagac tacgacggta ggccgttatt actatgctat ggactactgg      720
```

```
ggccaaggga ccacggtcac cgtctcctcc ggaggtggtg gatccgatat caaactgcag    780
cagtcagggg ctgaactggc aagacctggg gcctcagtga agatgtcctg caagacttct    840
ggctacacct ttactaggta cacgatgcac tgggtaaaac agaggcctgg acagggtctg    900
gaatggattg gatacattaa tcctagccgt ggttatacta attacaatca gaagttcaag    960
gacaaggcca cattgactac agacaaatcc tccagcacag cctacatgca actgagcagc   1020
ctgacatctg aggactctgc agtctattac tgtgcaagat attatgatga tcattactgc   1080
cttgactact ggggccaagg caccactctc acagtctcct cagtcgaagg tggaagtgga   1140
ggttctggtg gaagtggagg ttcaggtgga gtcgacgaca ttcagctgac ccagtctcca   1200
gcaatcatgt ctgcatctcc aggggagaag gtcaccatga cctgcagagc cagttcaagt   1260
gtaagttaca tgaactggta ccagcagaag tcaggcaccc cccccaaaag atggatttat   1320
gacacatcca aagtggcttc tggagtccct tatcgcttca gtggcagtgg gtctgggacc   1380
tcatactctc tcacaatcag cagcatggag gctgaagatg ctgccactta ttactgccaa   1440
cagtggagta gtaacccgct cacgttcggt gctgggacca agctggagct gaaa         1494
```

<210> SEQ ID NO 3
<211> LENGTH: 124
<212> TYPE: PRT
<213> ORGANISM: Artificial Sequence
<220> FEATURE:
<223> OTHER INFORMATION: VH anti CD19

<400> SEQUENCE: 3

```
Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
                100                 105                 110

Tyr Trp Gly Gln Gly Thr Thr Val Thr Val Ser Ser
            115                 120
```

<210> SEQ ID NO 4
<211> LENGTH: 372
<212> TYPE: DNA
<213> ORGANISM: Artificial Sequence
<220> FEATURE:
<223> OTHER INFORMATION: VH anti CD19

<400> SEQUENCE: 4

```
caggtgcagc tgcagcagtc tggggctgag ctggtgaggc ctgggtcctc agtgaagatt     60
tcctgcaagg cttctggcta tgcattcagt agctactgga tgaactgggt gaagcagagg    120
cctggacagg gtcttgagtg gattggacag atttggcctg gagatggtga tactaactac    180
aatggaaagt tcaagggtaa agccactctg actgcagacg aatcctccag cacagcctac    240
```

```
atgcaactca gcagcctagc atctgaggac tctgcggtct atttctgtgc aagacgggag    300
actacgacgg taggccgtta ttactatgct atggactact ggggccaagg gaccacggtc    360
accgtctcct cc                                                         372
```

<210> SEQ ID NO 5
<211> LENGTH: 111
<212> TYPE: PRT
<213> ORGANISM: Artificial Sequence
<220> FEATURE:
<223> OTHER INFORMATION: VL anti CD19

<400> SEQUENCE: 5

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys
            100                 105                 110
```

<210> SEQ ID NO 6
<211> LENGTH: 333
<212> TYPE: DNA
<213> ORGANISM: Artificial Sequence
<220> FEATURE:
<223> OTHER INFORMATION: VL anti CD19

<400> SEQUENCE: 6

```
gatatccagc tgacccagtc tccagcttct ttggctgtgt ctctagggca gagggccacc    60
atctcctgca aggccagcca agtgttgat tatgatggtg atagttattt gaactggtac    120
caacagattc caggacagcc acccaaactc ctcatctatg atgcatccaa tctagtttct    180
gggatcccac ccaggtttag tggcagtggg tctgggacag acttcaccct caacatccat    240
cctgtggaga aggtggatgc tgcaacctat cactgtcagc aaagtactga ggatccgtgg    300
acgttcggtg agggaccaa gctcgagatc aaa                                  333
```

<210> SEQ ID NO 7
<211> LENGTH: 119
<212> TYPE: PRT
<213> ORGANISM: Artificial Sequence
<220> FEATURE:
<223> OTHER INFORMATION: VH anti CD3

<400> SEQUENCE: 7

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
```

```
            50                  55                  60
Lys Asp Lys Ala Thr Leu Thr Thr Asp Lys Ser Ser Thr Ala Tyr
 65                  70                  75                  80

Met Gln Leu Ser Ser Leu Thr Ser Glu Asp Ser Ala Val Tyr Cys
                     85                  90                  95

Ala Arg Tyr Tyr Asp Asp His Tyr Cys Leu Asp Tyr Trp Gly Gln Gly
                100                 105                 110

Thr Thr Leu Thr Val Ser Ser
            115
```

<210> SEQ ID NO 8
<211> LENGTH: 357
<212> TYPE: DNA
<213> ORGANISM: Artificial Sequence
<220> FEATURE:
<223> OTHER INFORMATION: VH anti CD3

<400> SEQUENCE: 8

```
gatatcaaac tgcagcagtc aggggctgaa ctggcaagac ctggggcctc agtgaagatg      60
tcctgcaaga cttctggcta cacctttact aggtacacga tgcactgggt aaaacagagg     120
cctggacagg gtctgaatg gattggatac attaatccta gccgtggtta tactaattac     180
aatcagaagt tcaaggacaa ggccacattg actacagaca atcctccag cacagcctac     240 atgcaactga gcagcctgac atctgaggac tctgcagtct attactgtgc aagatattat     300
gatgatcatt actgccttga ctactggggc caaggcacca ctctcacagt ctcctca       357
```

<210> SEQ ID NO 9
<211> LENGTH: 106
<212> TYPE: PRT
<213> ORGANISM: Artificial Sequence
<220> FEATURE:
<223> OTHER INFORMATION: VL anti CD3

<400> SEQUENCE: 9

```
Asp Ile Gln Leu Thr Gln Ser Pro Ala Ile Met Ser Ala Ser Pro Gly
 1               5                  10                  15

Glu Lys Val Thr Met Thr Cys Arg Ala Ser Ser Ser Val Ser Tyr Met
                20                  25                  30

Asn Trp Tyr Gln Gln Lys Ser Gly Thr Ser Pro Lys Arg Trp Ile Tyr
            35                  40                  45

Asp Thr Ser Lys Val Ala Ser Gly Val Pro Tyr Arg Phe Ser Gly Ser
        50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105
```

<210> SEQ ID NO 10
<211> LENGTH: 318
<212> TYPE: DNA
<213> ORGANISM: Artificial Sequence
<220> FEATURE:
<223> OTHER INFORMATION: VL anti CD3

<400> SEQUENCE: 10

```
gacattcagc tgacccagtc tccagcaatc atgtctgcat ctccagggga gaaggtcacc      60
```

-continued

```
atgacctgca gagccagttc aagtgtaagt tacatgaact ggtaccagca gaagtcaggc    120
acctccccca aaagatggat ttatgacaca tccaaagtgg cttctggagt cccttatcgc    180
ttcagtggca gtgggtctgg gacctcatac tctctcacaa tcagcagcat ggaggctgaa    240
gatgctgcca cttattactg ccaacagtgg agtagtaacc cgctcacgtt cggtgctggg    300
accaagctgg agctgaaa                                                  318
```

<210> SEQ ID NO 11
<211> LENGTH: 10
<212> TYPE: PRT
<213> ORGANISM: artificial
<220> FEATURE:
<223> OTHER INFORMATION: CD3 CDR-H1

<400> SEQUENCE: 11

Gly Tyr Thr Phe Thr Arg Tyr Thr Met His
1               5                   10

<210> SEQ ID NO 12
<211> LENGTH: 17
<212> TYPE: PRT
<213> ORGANISM: artificial
<220> FEATURE:
<223> OTHER INFORMATION: CD3 CDR-H2

<400> SEQUENCE: 12

Tyr Ile Asn Pro Ser Arg Gly Tyr Thr Asn Tyr Asn Gln Lys Phe Lys
1               5                   10                  15

Asp

<210> SEQ ID NO 13
<211> LENGTH: 10
<212> TYPE: PRT
<213> ORGANISM: artificial
<220> FEATURE:
<223> OTHER INFORMATION: CD3 CDR-H3

<400> SEQUENCE: 13

Tyr Tyr Asp Asp His Tyr Cys Leu Asp Tyr
1               5                   10

<210> SEQ ID NO 14
<211> LENGTH: 10
<212> TYPE: PRT
<213> ORGANISM: artificial
<220> FEATURE:
<223> OTHER INFORMATION: CD3 CDR-L1

<400> SEQUENCE: 14

Arg Ala Ser Ser Ser Val Ser Tyr Met Asn
1               5                   10

<210> SEQ ID NO 15
<211> LENGTH: 7
<212> TYPE: PRT
<213> ORGANISM: artificial
<220> FEATURE:
<223> OTHER INFORMATION: CD3 CDR-L2

<400> SEQUENCE: 15

Asp Thr Ser Lys Val Ala Ser
1               5

<210> SEQ ID NO 16

```
<211> LENGTH: 9
<212> TYPE: PRT
<213> ORGANISM: artificial
<220> FEATURE:
<223> OTHER INFORMATION: CD3 CDR-L3

<400> SEQUENCE: 16

Gln Gln Trp Ser Ser Asn Pro Leu Thr
1               5

<210> SEQ ID NO 17
<211> LENGTH: 10
<212> TYPE: PRT
<213> ORGANISM: artificial
<220> FEATURE:
<223> OTHER INFORMATION: CD19 CDR-H1

<400> SEQUENCE: 17

Gly Tyr Ala Phe Ser Ser Tyr Trp Met Asn
1               5                   10

<210> SEQ ID NO 18
<211> LENGTH: 17
<212> TYPE: PRT
<213> ORGANISM: artificial
<220> FEATURE:
<223> OTHER INFORMATION: CD19 CDR-H2

<400> SEQUENCE: 18

Gln Ile Trp Pro Gly Asp Gly Asp Thr Asn Tyr Asn Gly Lys Phe Lys
1               5                   10                  15

Gly

<210> SEQ ID NO 19
<211> LENGTH: 15
<212> TYPE: PRT
<213> ORGANISM: artificial
<220> FEATURE:
<223> OTHER INFORMATION: CD19 CDR-H3

<400> SEQUENCE: 19

Arg Glu Thr Thr Thr Val Gly Arg Tyr Tyr Tyr Ala Met Asp Tyr
1               5                   10                  15

<210> SEQ ID NO 20
<211> LENGTH: 15
<212> TYPE: PRT
<213> ORGANISM: artificial
<220> FEATURE:
<223> OTHER INFORMATION: CD19 CDR-L1

<400> SEQUENCE: 20

Lys Ala Ser Gln Ser Val Asp Tyr Asp Gly Asp Ser Tyr Leu Asn
1               5                   10                  15

<210> SEQ ID NO 21
<211> LENGTH: 7
<212> TYPE: PRT
<213> ORGANISM: artificial
<220> FEATURE:
<223> OTHER INFORMATION: CD19 CDR-L2

<400> SEQUENCE: 21

Asp Ala Ser Asn Leu Val Ser
1               5
```

```
<210> SEQ ID NO 22
<211> LENGTH: 9
<212> TYPE: PRT
<213> ORGANISM: artificial
<220> FEATURE:
<223> OTHER INFORMATION: CD19 CDR-L3

<400> SEQUENCE: 22

Gln Gln Ser Thr Glu Asp Pro Trp Thr
1               5

<210> SEQ ID NO 23
<211> LENGTH: 5
<212> TYPE: PRT
<213> ORGANISM: Artificial Sequence
<220> FEATURE:
<223> OTHER INFORMATION: Spacer

<400> SEQUENCE: 23

Gly Gly Gly Gly Ser
1               5

<210> SEQ ID NO 24
<211> LENGTH: 5
<212> TYPE: PRT
<213> ORGANISM: artificial
<220> FEATURE:
<223> OTHER INFORMATION: CD3 CDR-H1

<400> SEQUENCE: 24

Arg Tyr Thr Met His
1               5

<210> SEQ ID NO 25
<211> LENGTH: 5
<212> TYPE: PRT
<213> ORGANISM: artificial
<220> FEATURE:
<223> OTHER INFORMATION: CD19 CDR-H1

<400> SEQUENCE: 25

Ser Tyr Trp Met Asn
1               5
```